(12) United States Patent
Hu et al.

(10) Patent No.: US 10,094,893 B2
(45) Date of Patent: Oct. 9, 2018

(54) MINIATURIZED MAGNETIC RESONANCE PROBE

(71) Applicant: The Regents of the University of California, Oakland, CA (US)

(72) Inventors: Jianping Hu, Los Angeles, CA (US); Louis Bouchard, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 766 days.

(21) Appl. No.: 14/413,679

(22) PCT Filed: Jul. 11, 2013

(86) PCT No.: PCT/US2013/050161
§ 371 (c)(1),
(2) Date: Jan. 8, 2015

(87) PCT Pub. No.: WO2014/011937
PCT Pub. Date: Jan. 16, 2014

(65) Prior Publication Data
US 2015/0137807 A1    May 21, 2015

Related U.S. Application Data

(60) Provisional application No. 61/670,736, filed on Jul. 12, 2012.

(51) Int. Cl.
*G01V 3/00* (2006.01)
*G01R 33/36* (2006.01)
(Continued)

(52) U.S. Cl.
CPC ......... *G01R 33/3628* (2013.01); *G01N 24/08* (2013.01); *G01N 24/10* (2013.01);
(Continued)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 6,306,590 B1 * 10/2001 Mehta ................. B01J 19/0093
422/68.1
2003/0090267 A1    5/2003 Rubashov
(Continued)

FOREIGN PATENT DOCUMENTS

RU         2171630 C2    8/2001
WO    WO 2010/095063 A1    8/2010

OTHER PUBLICATIONS

International Search Report for International Application No. PCT/US2013/050161 dated Nov. 7, 2013.

*Primary Examiner* — Water L Lindsay, Jr.
*Assistant Examiner* — Frederick Wenderoth
(74) *Attorney, Agent, or Firm* — Knobbe Martens Olson & Bear, LLP

(57) ABSTRACT

Described herein are a magnetic resonance probe and a NMR, MRI, or EPR apparatus including the same. The magnetic resonance probe includes a conductor electrically coupled to the resonator and configured to transmit and receive electromagnetic radiation to and from a sample, wherein the conductor includes one or more cascaded narrowed regions along its longitudinal dimension and a slot within one of the one or more cascaded narrowed regions; and an electrical circuit coupled to the conductor and the resonator.

51 Claims, 29 Drawing Sheets

(51) Int. Cl.
| | |
|---|---|
| *G01N 24/08* | (2006.01) |
| *G01N 24/10* | (2006.01) |
| *G01R 33/30* | (2006.01) |
| *G01R 33/34* | (2006.01) |
| *G01R 33/465* | (2006.01) |
| *G01R 33/60* | (2006.01) |
| *G01N 33/483* | (2006.01) |
| *G01R 33/3415* | (2006.01) |

(52) U.S. Cl.
CPC ......... *G01N 33/483* (2013.01); *G01R 33/302* (2013.01); *G01R 33/34092* (2013.01); *G01R 33/465* (2013.01); *G01R 33/60* (2013.01); *G01R 33/3415* (2013.01)

(58) Field of Classification Search
USPC ........................................................ 324/307
See application file for complete search history.

(56) References Cited

U.S. PATENT DOCUMENTS

| | | | | |
|---|---|---|---|---|
| 2005/0122115 | A1* | 6/2005 | Maguire | G01R 33/345 324/322 |
| 2006/0250133 | A1 | 11/2006 | Krieg et al. | |
| 2007/0055127 | A1 | 3/2007 | Ladebeck et al. | |
| 2009/0261241 | A1* | 10/2009 | Roukes | B82Y 15/00 250/282 |
| 2010/0321017 | A1* | 12/2010 | Pines | G01R 33/302 324/309 |
| 2012/0122084 | A1* | 5/2012 | Wagner | C12N 5/0612 435/6.1 |

\* cited by examiner

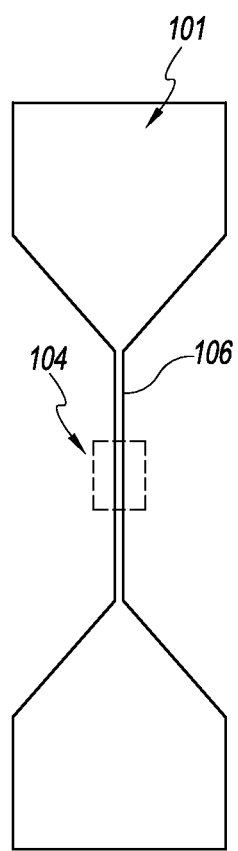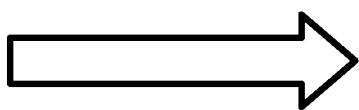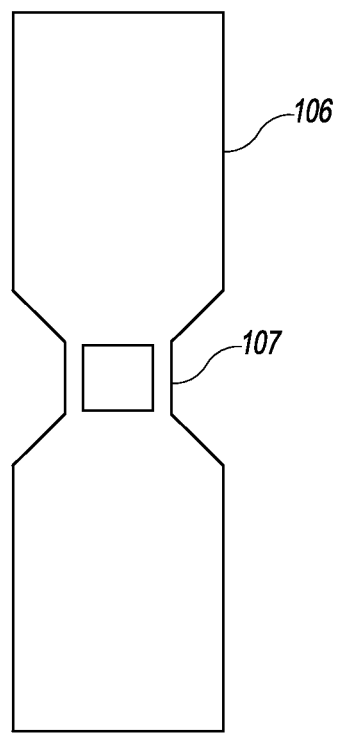
FIG. 1D  FIG. 1E

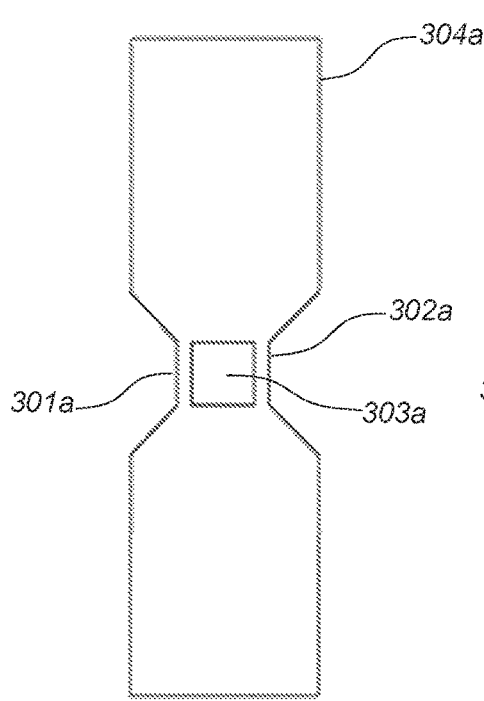
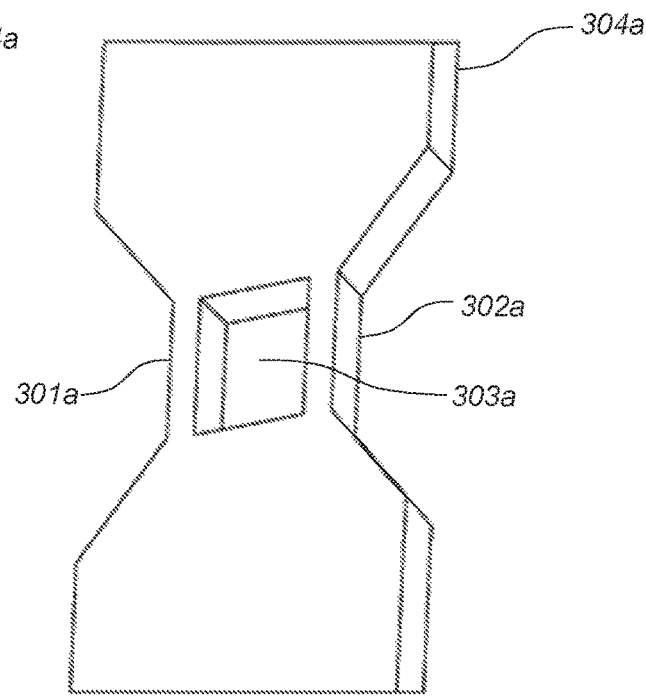
FIG. 3A
FIG. 3B
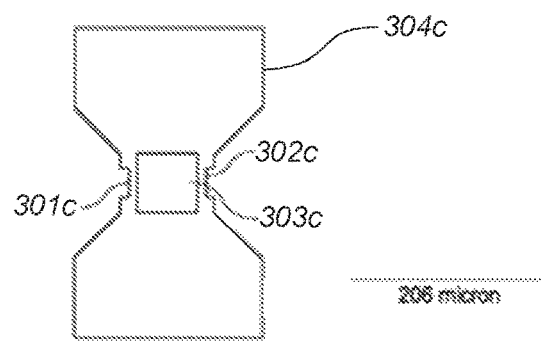
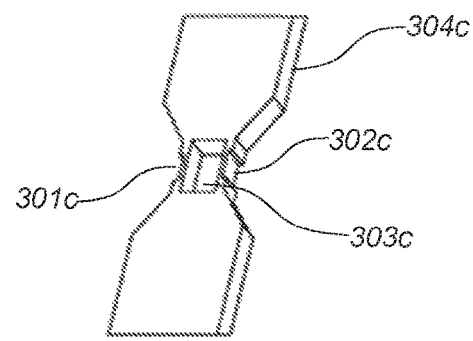
FIG. 3C
FIG. 3D 206 micron 206 micron

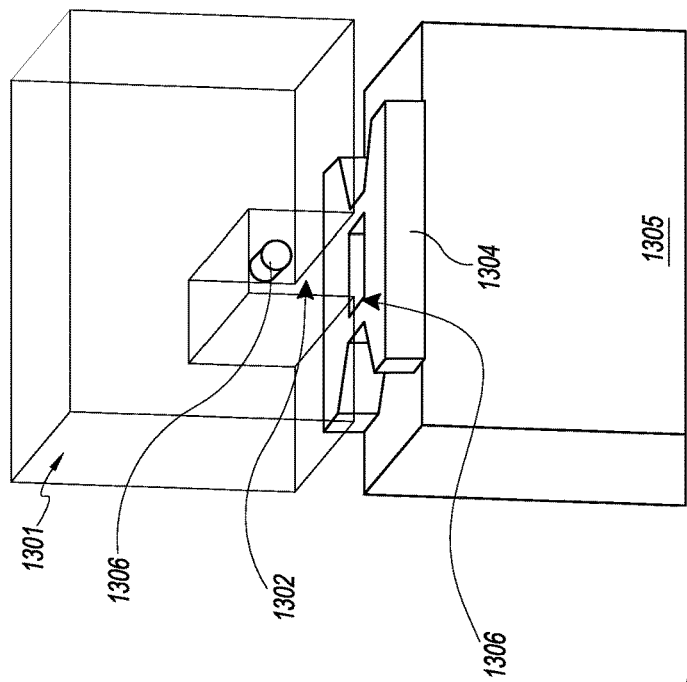
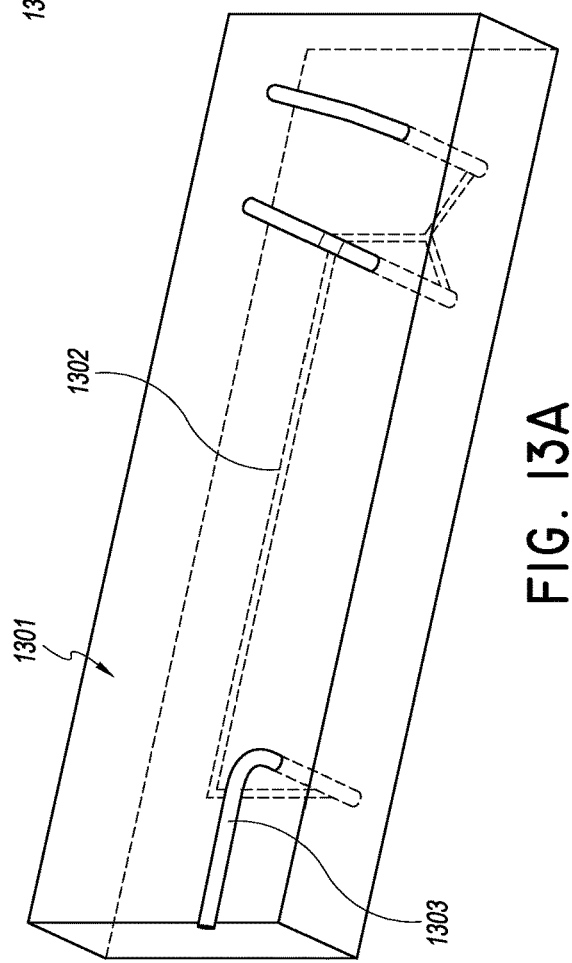
FIG. 13B
FIG. 13A

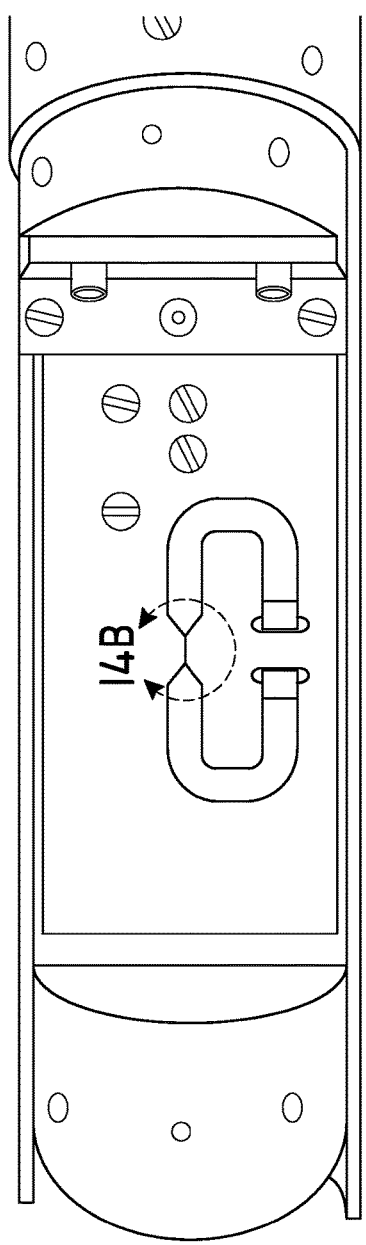
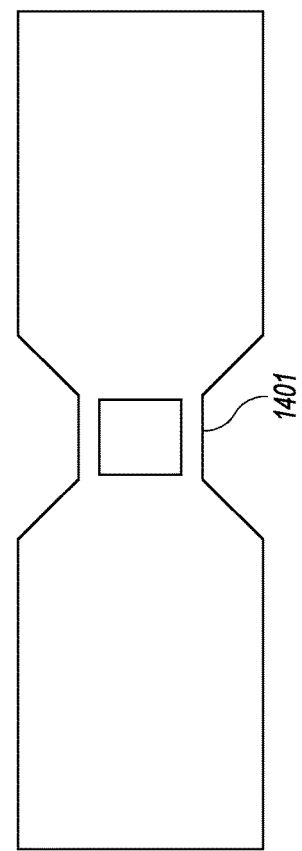
FIG. 14A
FIG. 14B

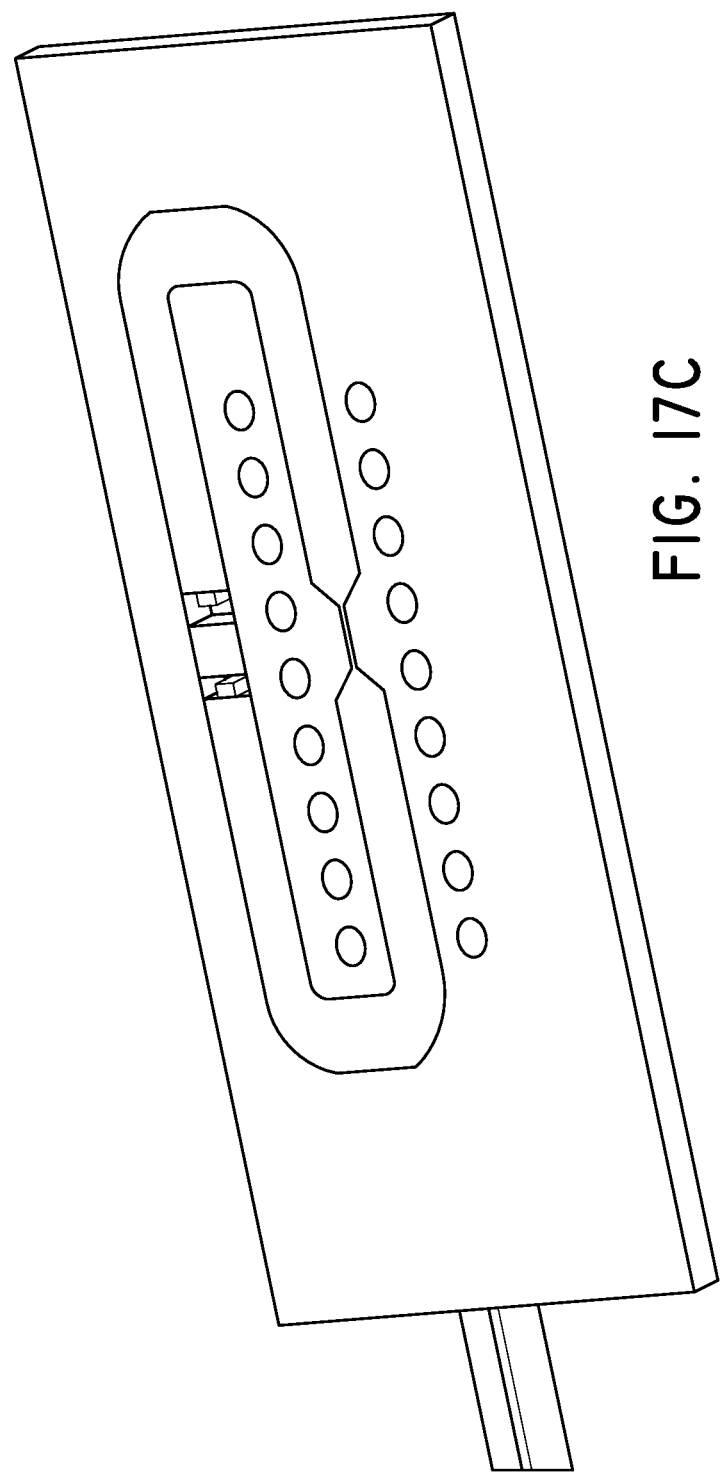

MINIATURIZED MAGNETIC RESONANCE PROBE

CROSS-REFERENCE TO RELATED APPLICATIONS

This application is the U.S. National Phase of International Application No. PCT/US2013/050161 entitled MINIATURIZED MAGNETIC RESONANCE PROBE, filed Jul. 11, 2013 and published on Jan. 16, 2014 as WO 2014/011937, which claims priority to U.S. Provisional Application No. 61/670,736, filed Jul. 12, 2012.

BACKGROUND

Field

The present disclosure relates to a magnetic resonance probe and a nuclear magnetic resonance (NMR), magnetic resonance imaging (MRI), or electron paramagnetic resonance (EPR) apparatus comprising the same. The present disclosure also relates to methods of detecting magnetic resonance using the same.

Description of the Related Art

Nuclear magnetic resonance (NMR) is a well-established spectroscopic technique for the identification of chemical species and is broadly applied in many different fields including synthetic and supramolecular chemistry, catalysis, materials science, biology and medicine. In a typical NMR experiment, the sample is exposed to a static magnetic ($B_0$) field. After excitation of the nuclear spin system using a short radio frequency (RF) pulse, the processing magnetization is detected. The recorded resonance frequencies (peaks in the NMR spectra) are a probe of the local electronic environment of a specific nucleus in a molecule. Additionally, fine structure such as J-couplings and dipolar couplings are a measure of chemical bonding and distance between two nuclei, respectively. NMR is a non-invasive technique and provides direct quantitative information.

Microcoils and microcoil array resonators have been used as detectors in microfluidic electromagnetic probes. However, the sensitivity, efficiency and the RF field homogeneity of these coils constitute a bottleneck for the development of the further applications of electromagnetic probes.

SUMMARY

Some embodiments described herein provide a magnetic resonance probe for use in a NMR, MRI, or EPR. The magnetic resonance probe includes a resonator; a conductor electrically coupled to the resonator and configured to transmit and receive electromagnetic radiation to and from a sample, wherein the conductor comprises one or more cascaded narrowed regions along its longitudinal dimension and a slot within one of the one or more cascaded narrowed regions; and an electrical circuit coupled to the conductor and the resonator.

In some embodiments, the constricted slot is positioned centered on the narrowest region of the conductor.

In some embodiments, the constricted slot is defined by a first wire and a second wire substantially parallel to its longitudinal dimension.

In some embodiments, the constricted slot is defined by a first wire and a second wire, the first and the second wires having one or more cascaded narrowed regions.

In some embodiments, the constricted slot is defined by a first wire and a second wire, the first and the second wires having one or more intrusions extending laterally inside the slot.

In some embodiments, the constricted slot is defined by a first wire and a second wire, the first and the second wires continuously intruding laterally inside the slot.

In some embodiments, the resonator is balanced.

In some embodiments, the magnetic resonance probe further comprises a ground plate adjacent to the conductor, wherein the ground plate has one or more perforations.

In some embodiments, the perforations are positioned around the conductor and spaced from the slot.

In some embodiments, the magnetic resonance probe further includes a shimming mechanism to reduce line-width of signal peaks.

In some embodiments, a narrowest region of the conductor has a lateral width in a range from about 10µ to 1000µ.

In some embodiments, a narrowest region of the slot has a lateral width in a range from about 10µ to 1000µ.

In some embodiments, a lateral width of the conductor at each cascaded narrowed region is decreased by from about 1% to about 90%.

In some embodiments, the probe is laminated to a printed circuit board.

In some embodiments, the magnetic resonance probe further comprises a plurality of resonators; a plurality of elongated conductors electrically coupled to the resonators and configured to transmit and receive electromagnetic radiation to and from one or more samples, wherein each conductor comprises one or more cascaded narrowed regions and a slot within one of the one or more cascaded narrowed regions; and an electrical circuit coupled to the conductors and resonators.

Some embodiments described herein provide a NMR, MRI, or EPR apparatus. The apparatus includes a magnetic resonance probe, wherein the probe comprises one or more resonators, one or more elongated conductors electrically coupled to the resonators and configured to transmit and receive electromagnetic radiation to and from one or more samples, wherein each conductor comprises two or more cascaded narrowed regions and a slot within one of the one or more cascaded narrowed regions, and an electrical circuit coupled to the conductors and resonators; and one or more microfluidic chips, wherein the microfluidic chip comprises one or more channels configured to transport a sample and is aligned with the slot.

In some embodiments, the apparatus further comprises a microfluidic element configured to drive a sample through the channels.

In some embodiments, the apparatus further comprises an automatic adjustment element configured to achieve a balanced magnetic field.

Some embodiments described herein provide a method of detecting magnetic resonance in a sample. The method includes providing a magnetic resonance probe comprising an elongated conductor, wherein the conductor has one or more cascaded narrowed regions along its longitudinal dimension and a slot within one of the one or more cascaded narrowed regions; positioning the sample inside or adjacent to the slot; applying an electrical excitation signal to energize the conductor; and detecting an electromagnetic signal emanating from the sample.

Some embodiments described herein provide a method of analyzing a sample. The method includes providing a magnetic resonance probe comprising an elongated conductor, wherein the conductor comprises one or more cascaded narrowed regions along its longitudinal dimension and a slot within one of the one or more cascaded narrowed regions; introducing the sample into a microfluidic chip, wherein the microfluidic chip comprises one or more channels configured to transport the sample and is positioned inside or adjacent to the slot; transporting the sample through the channels of the microfluidic chip; applying an electromagnetic excitation signal to energize the conductor; and detecting an electromagnetic signal emanating from the sample.

In some embodiments, the electromagnetic signal emanating from the sample is used to identify the presence of a cancer cell.

In some embodiments, the microfluidic chip is aligned with the slot either manually or automatically.

BRIEF DESCRIPTION OF THE DRAWINGS

FIGS. 1A through 1E illustrate examples of a constricted slot magnetic resonance probe. (1A) Cross-section of the microstrip in the detector. (1B) Constricted slot. (1C) Expanded view of the constricted slot. (1D) Two constrictions with constricted slot in the middle of the microstrip. (E) A close-up view of the constricted slot (dotted region indicated in 1D).

FIGS. 3A through 3D illustrate examples of the cascaded constricted slot variant with outer trimming. (3A) and (3B): First order constricted slot. (3C) and (3D): Second order constricted slot (i.e. first order constricted slot with outer trimming added).

FIGS. 13A through 13D illustrate examples of the single resonance microfluidic NMR system. (13A) The microfluidic chip. (13B) The detailed cross-section view of the constricted section. (13C) The front view of the NMR system. (13D) 3D view of the system.

FIGS. 14A and 14B illustrates an example of the top view of the laminate. (14A) shows the top view of the RF probe head, illustrating the stripline and its constriction. The dotted circled region shown corresponds to the section shown in FIG. 1D. (14B) Expanded view over the constricted slot (same as FIG. 1E).

FIGS. 17A through 17C illustrate examples of the laminate of the microfluidic NMR probe. (17A) The front view of the laminate. (17B) The back view of the laminate. (17C) Perspective view of the laminate showing the front view, on top of which we have indicated the position of the ground plate perforations (on the back plane).

DETAILED DESCRIPTION OF THE PREFERRED EMBODIMENT

Figure 1B:
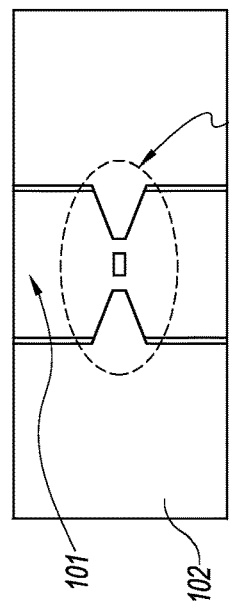

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The measurement of NMR signals from small amounts of sample and small volumes requires high efficiency, high sensitivity, low noise and focused RF fields in the detection region where the sample is located only in the focused region. Minimization of the fields in the detection region is also desirable for nondestructive measurements in biological samples or solution state NMR. Printed circuit board (PCB)- based NMR probes provides one system to meet these requirements. Variants which are printed directly onto a microfluidic chip are also possible.

Some embodiments include a magnetic resonance probe with a constricted slot-based conductor providing an ultra small detection region and a radiofrequency magnetic field balanced and confined to the ultra small region. This probe yields a high filling factor and high sensitivity. An optional noise mitigation mechanism can be built-in to further improve the signal to noise ratio (SNR) and limit of detection (LOD) of this probe. In some embodiments, a planar configuration of the probe can enable a wide range of applications in microfluidics, surface measurements, or measurements made of films. Thus it can be used to investigate chemical and structural properties of ultra small volume samples in chemical, biomedical and materials sciences. It is especially suitable for the rapid measurement of time sensitive samples that are found in small quantities such as biological cells, thin films or for costly chemical and biochemical reagents. For example, in some embodiments, the probe can be used to detect magnetic resonance signals from 2.5 pmol (picomoles) protons in a 50 micrometer region using a single scan.

Due to its high sensitivity, the magnetic resonance probe with a constricted slot-based conductor can be used in wide range of applications from biomedicine to chemistry and materials sciences. For instance, the probe can be used to measure a single cell and detect the presence of cancer cell or monitor cancer therapy. The probe can also be used for analysis of soft materials, biological cells (including small cluster of cells), or tissue samples (such as biopsies or histologic sections). Moreover, the probe may also be used for analysis of chemicals, analytes (biological or chemical) including trace amounts of substances, as well as chemical reactions. Further, the probe may also be used for analysis of solid (hard) materials, including surfaces, wafers, particles, films, heterostructures or electronic devices. Additional use of the probe also includes classical or quantum computing applications, whereby media located in different regions of space are addressed independently using tailored RF waveforms.

The magnetic resonance probe is described herein to be used with the NMR, but the application of the magnetic resonance probe is not limited to NMR. The probe described herein can be used in a variety of devices that detect magnetic resonance. Examples include but are not limited to a NMR, magnetic resonance imaging (MRI), or electron paramagnetic resonance (EPR).

The terms "constriction" and "narrowed regions," as used herein, may be used interchangeably.

Some embodiments relate to an electromagnetic field detector for use in a NMR, MRI, or EPR probe. The detector includes a resonator, a conductor electrically coupled to the resonator and configured to transmit radiation to a sample, wherein the conductor comprises one or more cascaded narrowed regions along its longitudinal dimension and a slot within one of the one or more cascaded narrowed regions; and an electrical circuit coupled to the conductor and the resonator.

Figure 1A:
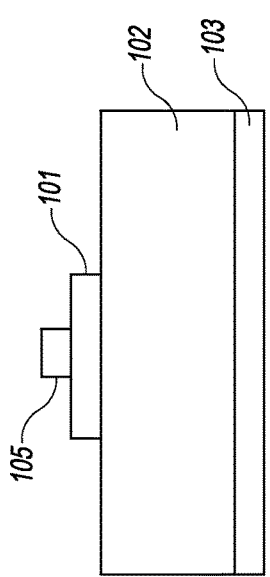
Figure 1C:
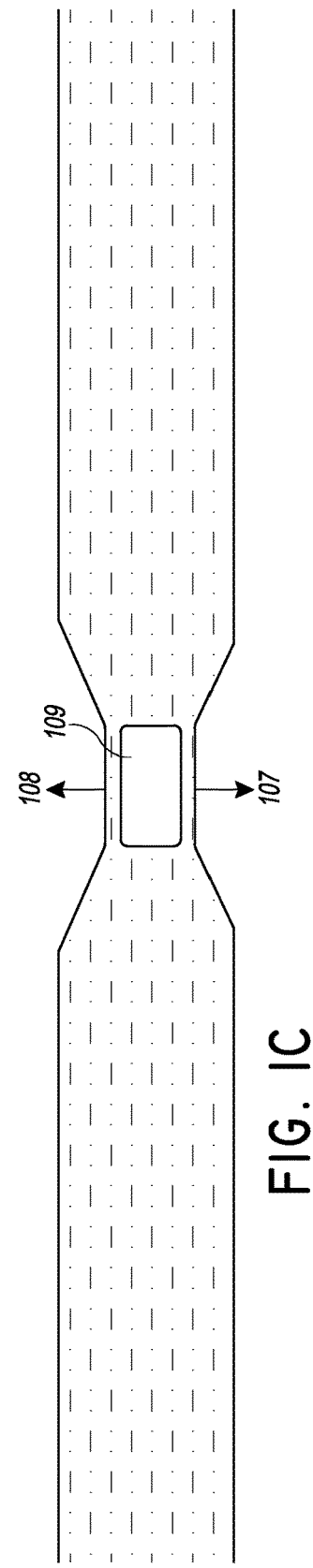

FIGS. 1A through 1E shows some embodiments of PCB-based NMR probes having a constricted slot detector. FIG. 1A is a cross-section view of the probe in the region of the constricted slot. FIGS. 1B and 1C show top views of two embodiments of constricted slots. FIG. 1D shows a larger view of the probe depicting an additional level of constriction 106. The slot 104 and constriction 107 are centered in the constriction 106 and depicted in FIG. 1E. In some embodiments, the region containing the constriction may also approximately overlap with the RF region and the sample region.

As shown in FIG. 1A, the NMR probe consists of a conductor 101, a substrate 102 and one ground 103. The sample 105 is placed adjacent to the conductor 101. As shown in FIG. 1B, the conductor 101 includes a constricted slot 104. The constricted slot advantageously generates a strong current density near the region of interest and focusing the RF field both in strength and spatial distribution.

FIG. 1C shows a top view of the constricted slot on the conductor. The conductor has a narrowed region along its longitudinal dimension in the region of the slot. A small, centrally located aperture 109 is cut out of the narrowed region of the conductor 101 to form the constricted slot 104. In FIG. 1C, a discontinuity is formed by the rectangular aperture cut into the conductor 101 such that the conductor 101 is connected on the two lateral sides of the aperture 109 by two "wires" forming the sides of the aperture 109. A first wire 107 and a second wire 108 form the lateral edges of the aperture 109 to define the constricted slot 104. The first and second wires can be substantially parallel to the longitudinal dimension of the constricted slot. The shape of the aperture can be rectangular, circular, stair-stepped, or any other shape. In some embodiments the aperture is symmetric.

FIG. 1D shows a top view of the conductor, and FIG. 1E is a close-up view of the of the region containing the constricted slot shown in FIG. 1D. As shown in FIG. 1D, the conductor 101 has a first constriction 106 and a constricted slot positioned in the center of the first constriction 106. A first constriction 106 can be formed by a first narrowings at locations longitudinally away from the region of the constricted slot. A second constriction 107 can be formed within the first constriction region 106 by further narrowing the lateral width of the first constriction 106. Further levels of cascading narrowings can be provided.

In some embodiments, the center of the narrowest constriction can overlap with the center of the constricted slot. In FIG. 1E, the second constriction 107 is formed in the region of the first constriction 106. The constricted slot 104 is located in the central region of the second constricted section 107, which is also the central region of the first constricted section 106. The central region of the conductor (trace) is used as the detection region. The second constriction 107 can be the sensitive region or detection region of the magnetic resonance probe. The use of the second constriction can improve level of sensitivity. The tapered narrowed regions shown in FIGS. 1B through 1E can reduce reflections of traveling waves and improve the efficiency and SNR of the NMR probe.

The substrate 102 can be formed of suitable dielectric materials, including but not limited to glass, ceramics, polymers such as Polydimethylsiloxane (PDMS), and silicon. In some embodiments, the substrate can be formed of glass. In some embodiments, the substrate can be formed of ceramics. In some embodiments, the substrate can be formed of silicon material.

The conductor 101 can be formed of suitable conducting materials, including but not limited to copper, silver, iron, aluminum, platinum, gold, indium tin oxide and other metals, alloys and conductive non-metals. In some embodiments, the conductor is formed of a metal. In some embodiments, the conductor is formed of copper.

The conductor 101 can be formed in different shapes. In some embodiments, the conductor can be an elongated strip of the type used in microstrip circuits. In some embodiments, the conductor can be a coil or a conductor material shaped into a pattern similar to the patterns shown. In some embodiments, the conductor can be a circular or substantially circular shape. In some embodiments, the conductor can be of a rectangular shape optionally with tapered or rounded corners.

The construction of the conductor and other components of the electromagnetic detector utilize common materials and well-established techniques, such as those usually employed in precision mechanical working (e.g., computer numerical control lathe and cutter, electric discharge machining, etc.) and in electronics (e.g., photolithography, chemical etching, wire bonding, doping control, etc.), although more sophisticated techniques, such as electroless plating (ELP) techniques, sputtering, or evaporation, possibly combined with stereolithography, can be usefully employed. For example, the larger narrowed regions may be realized by standard wet etching techniques and smaller constrictions and finer details (e.g., the slot) can be refined or realized by laser etching.

Figure 2:
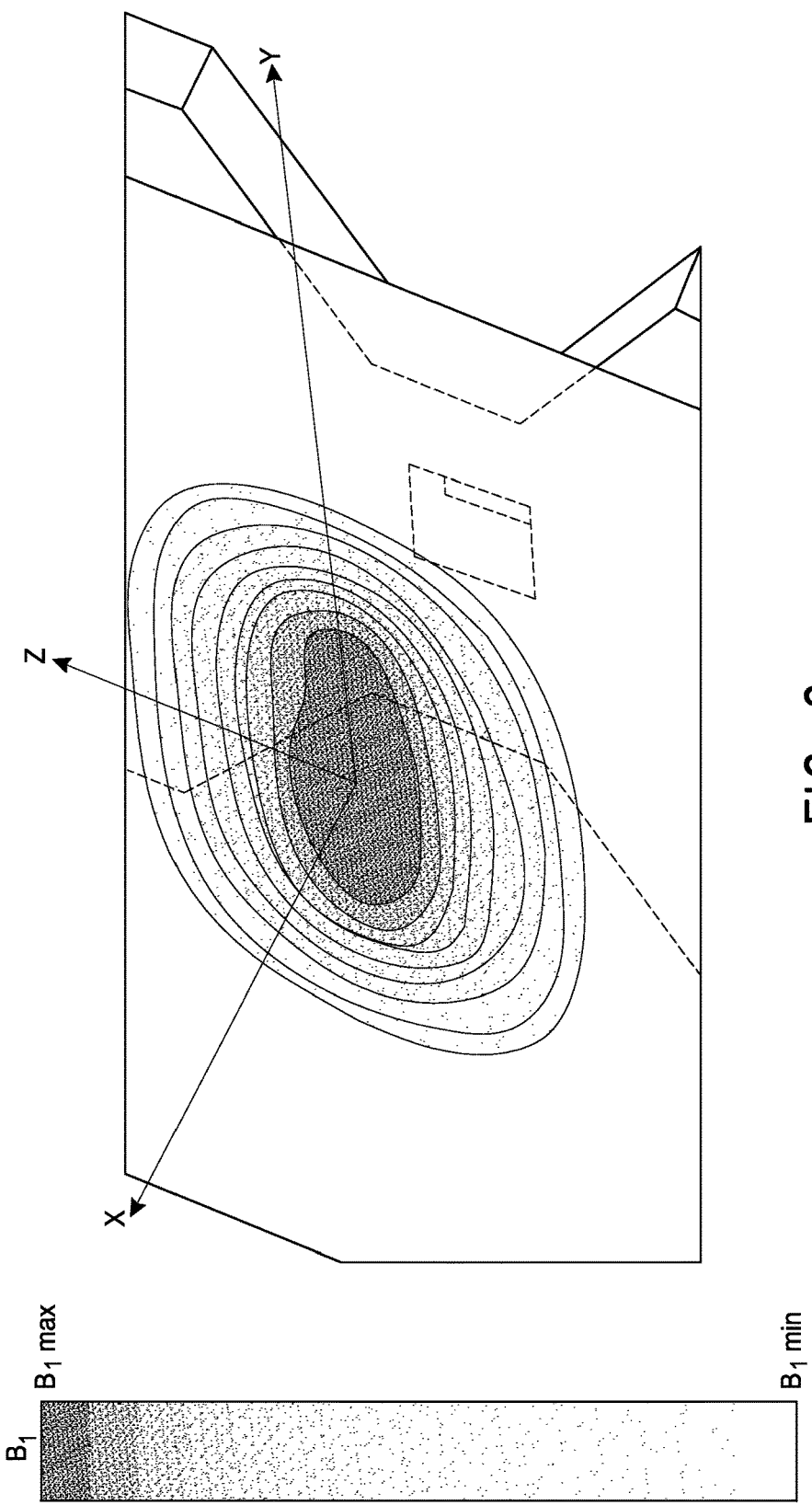
FIG. 2 illustrates an example of $B_1$ field (RF field) distributions at the sample center in the constricted slot probe (above the slot of the second constriction). The constriction shown by dotted lines is the same as that shown in FIG. 1E.

FIG. 2 shows the $B_1$ field distributions at sample center height in the constricted slot NMR detector. The $B_1$ field is $B_{xy}$, which is the vector addition of the $B_x$ field (along the X axis) and the $B_y$ field (along Y axis). In FIG. 2, the $B_1$ field is well confined to the constricted slot region. The detection region is adjacent to the constricted slot region. For example, the length of the detection region can be about 80 μm of the length of the constricted slot is 50 μm. The constricted slot structure can provide a confined RF magnetic field region. This confined region features a more intense RF magnetic field than in surrounding regions and also provide an ultra small detection region. In one example of the detection region, the RF magnetic field intensity changes by about 8% over a distance of 0.125 m along the longitudinal path of the conductor. Thus, the constricted slot probe can offer an advantage of measuring signals over smaller regions. The focusing of the RF magnetic field and field homogeneity can be adjusted by changing the configuration of the constricted slot.

As noted above, the conductor can include one or more constrictions in cascade. The addition of constrictions may help improve the strength and homogeneity of the RF field. In some embodiments, some of these cascaded constrictions are located within the region of the aperture (slot). FIGS. 3A through 3D show cascaded constrictions in the region of the slot achieved by outer trimming of the slot edges. FIG. 3A shows a top view of a first order constricted slot and FIG. 3B shows a side view of a first order constricted slot. The conductor is in an elongated shape and has one constriction centered on the strip. A constricted slot is formed in the first constriction region. FIG. 3C shows a top view of a second order constricted slot and FIG. 3D shows a side view of a second order constricted slot. In FIG. 3C, two constrictions are formed on the conductor in cascade. The lateral width of the second constriction is smaller than the first constriction, and the vertical length of the second constriction is shorter than the first constriction. The second constriction covers a smaller area than the first constriction. The aperture 303 is cut through both the first and the second constriction areas. The first wire 301 and the second wire 302 form the edges aperture 303 to define the constricted slot. The cascaded constriction is formed by trimming portions of the first and second wires from the side facing away from the aperture.

Figures 4A, 4B:
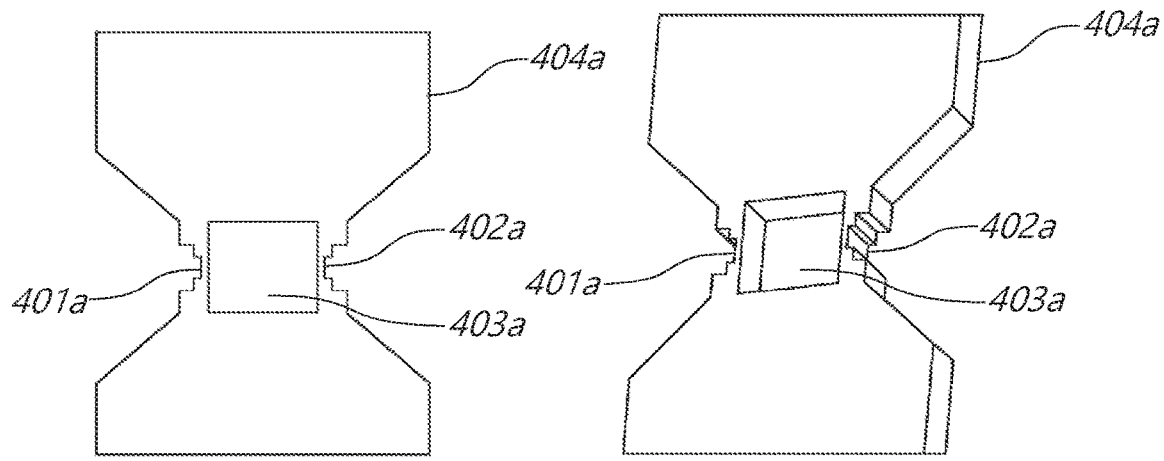
FIGS. 4A through 4D show additional examples of the cascaded constricted slot with additional outer trimming. (4A) and (4B): Third order constricted slot. (4C) and (4D): Fourth order constricted slot.
Figures 4C, 4D:
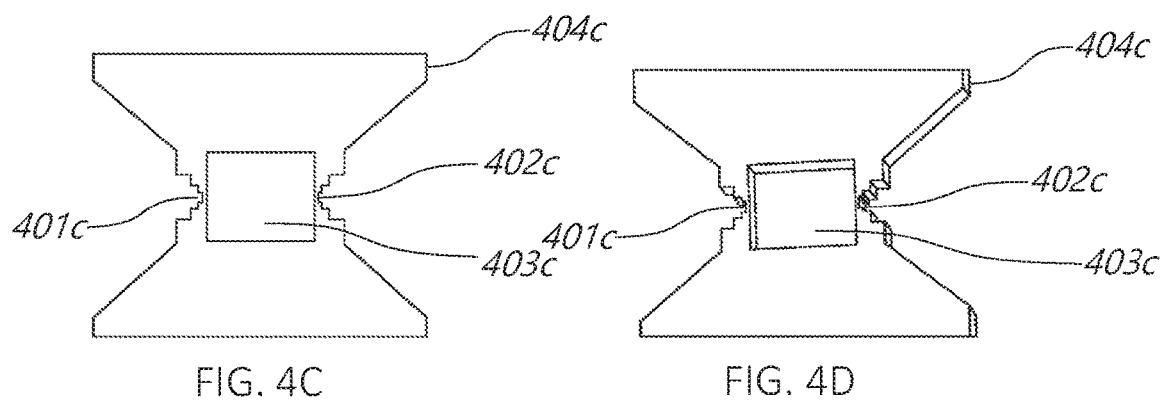

FIGS. 4A through 4D show additional examples of the cascaded constricted slot with outer trimming. FIG. 4A shows a top view of a third order constricted slot and FIG. 4B shows a perspective view of a third order constricted slot. In FIG. 4A, three constrictions are formed on the conductor in cascade. The lateral width of the first, second, and third constrictions are decreasing in that order. The vertical length of the first, second, and third constrictions are decreasing in that order. The area size of the first, second, and third constrictions are also becoming smaller in that order. An aperture is cut through the three constriction areas. The first wire and the second wire form the edges of the aperture to define the constricted slot. The second and third constrictions are formed by trimming portions of the first and second wires from the side facing away from the aperture. FIG. 4C shows a top view of a fourth order constricted slot and FIG. 4D shows a perspective view of a fourth order constricted slot. The conductor in FIG. 4C has one more constriction than the one in FIG. 4A, and the fourth constriction is formed by trimming additional portions of the first and second wires from the side facing away from the aperture. The RF magnetic field at the slot (detection region) becomes stronger when the order of cascade increases.

Figures 5A, 5B:
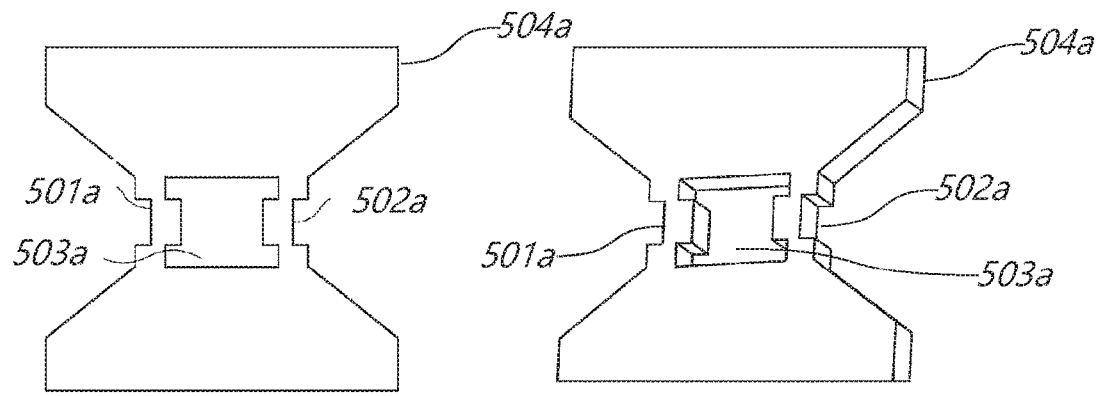
FIGS. 5A through 5D show examples of the cascaded constricted slot with outer trimming and intrusion. (5A) and (5B): Second order constricted slot. (5C) and (5D): Third order constricted slot.
Figures 5C, 5D:
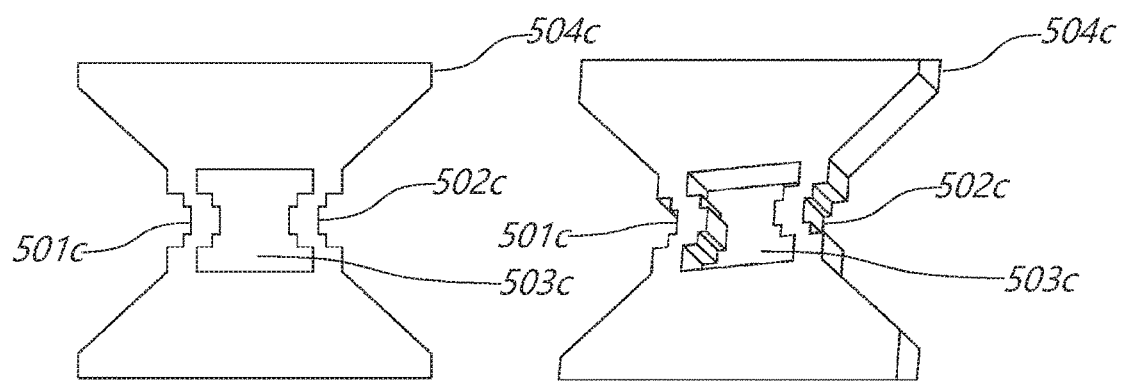

FIGS. 5A through 5D show examples of the cascaded constricted slot with outer trimming and intrusion into the interior of the slot. FIG. 5A shows a top view of a second order constricted slot and FIG. 5B shows a perspective view of a second order constricted slot. In FIG. 5A, two constrictions are formed on the conductor in cascade. The lateral width of the second constriction is smaller than the first constriction, and the vertical length of the second constriction is shorter than the first constriction. The second constriction covers a smaller area than the first constriction. The aperture 503 is cut through both the first and the second constriction areas. The first wire 501 and the second wire 502 form the edges of the aperture 503 to define the constricted slot. The shape of the aperture 503 is cut such that the first 501 and second 502 wires form in intrusion into the interior of the aperture 503. In the second constriction region, the first and second wires are trimmed from the side facing away from the aperture. FIG. 5C shows a top view of a third order constricted slot and FIG. 5D shows a perspective view of a third order constricted slot. The third order constricted slot is formed on the basis of the second order constricted slot shown in FIG. 5A by trimming the first and second wires one more time from the side facing away from the aperture and cutting the aperture such that an additional intrusion into the aperture of each of the first and the second wires is formed.

Accordingly, in some embodiments of cascaded constrictions, the two wires forming the edges of the slot are trimmed and slot is cut so as to keep the width of wire constant. In some alternative embodiments, rather than forming the intrusions by cutting a specific shaped slot, the intrusions are added after the slot is cut. The RF magnetic field at the slot and the detection region become stronger when the order of cascade increases.

Figures 6A, 6B:
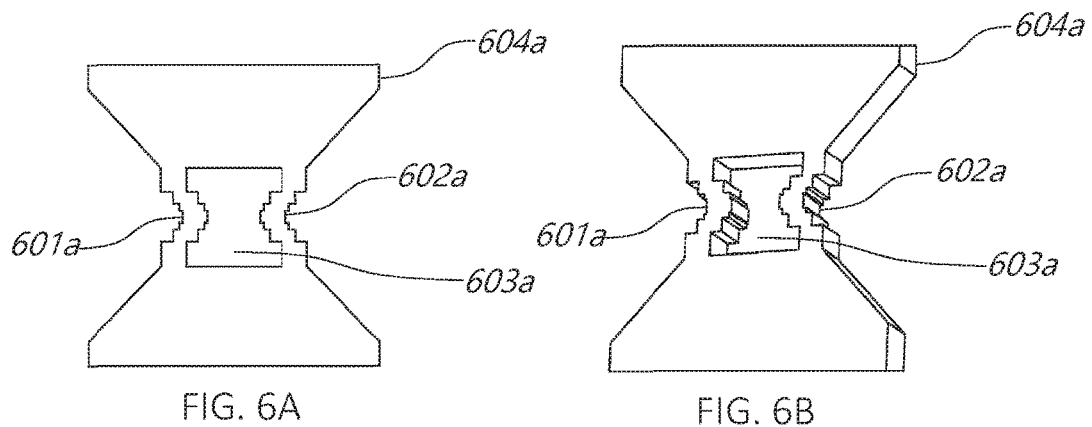
FIGS. 6A through 6D show examples of the cascaded constricted slot with outer trimming and intrusion. (6A) and (6B): Fourth order constricted slot. (6C) and (6D): Continuous constricted slot, which is a continuous extension of the fourth order constricted slot (i.e. the infinite order limit).
Figures 6C, 6D:
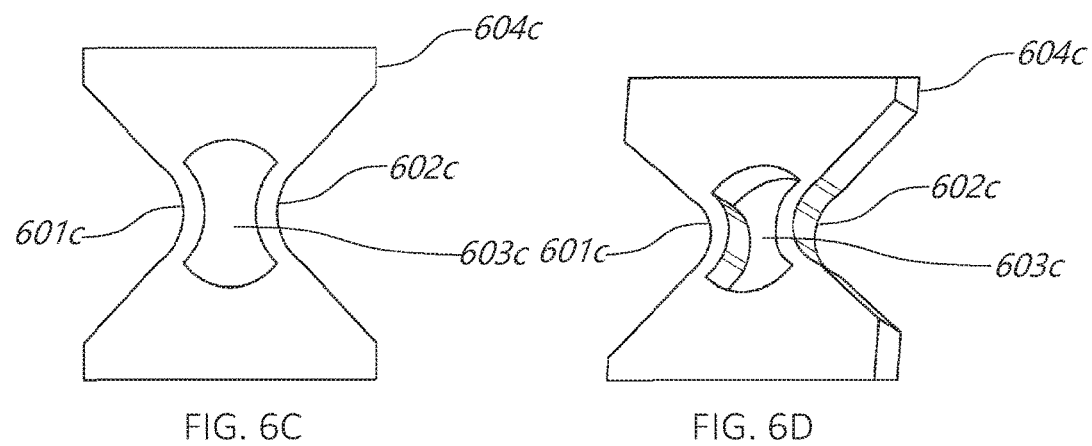

FIGS. 6A through 6D show additional examples of the cascaded constrictions with outer trimming and intrusions. FIG. 6A shows a top view of a fourth order constricted slot and FIG. 6B shows a perspective view of a fourth order constricted slot. The fourth order constricted slot in FIG. 6A is formed on the basis of the third order constricted slot shown in FIG. 5C by trimming the first and second wires one more time from the side facing away from the aperture and by forming another intrusion on each of the first and the second wires from the side facing the aperture. FIG. 6C shows a top view of a continuously constricted slot and FIG. 6D shows a perspective view of a continuously constricted slot. The continuously constricted slot may be converted from the fourth order or even higher order of constricted slot with outer and inner trimmings of the wires (e.g., such as by laser etching). The conductor in FIGS. 6A and 6C have the same RF magnetic field strength while the smooth transition of the curvature in FIG. 6C can reduce signal reflections and improve the efficiency and SNR. Thus, the efficiency and SNR can be improved by converting the stepped constricted slot to a smooth constricted slot.

The lateral dimension of the narrowest region of the conductor may vary depending on the size of the desired sample or the desired sensitivity. In some embodiments, the narrowest region of the conductor can have a lateral width in a range of about 1μ to about 1000μ. In some embodiments, the narrowest region of the conductor can have a lateral width in a range of about 1μ to about 500μ. In some embodiments, the narrowest region of the conductor can have a lateral width in a range of about 1μ to about 300μ. In some embodiments, the narrowest region of the conductor can have a lateral width in a range of about 1μ to about 200μ. In some embodiments, the narrowest region of the conductor can have a lateral width in a range of about 1μ to about 100μ. In some embodiments, the narrowest region of the conductor can have a lateral width in a range of about 1μ to about 50μ. In some embodiments, the narrowest region of the conductor can have a lateral width in a range of about 1μ to about 30μ. In some embodiments, the narrowest region of the conductor can have a lateral width in a range of about 1μ to about 20μ. In some embodiments, the narrowest region of the conductor can have a lateral width in a range of about 1μ to about 10μ. In some embodiments, the narrowest region of the conductor can have a lateral width in a range of about 10μ to about 1000μ. In some embodiments, the narrowest region of the conductor can have a lateral width in a range of about 10μ to about 500μ. In some embodiments, the narrowest region of the conductor can have a lateral width in a range of about 10μ to about 300μ. In some embodiments, the narrowest region of the conductor can have a lateral width in a range of about 10μ to about 200μ. In some embodiments, the narrowest region of the conductor can have a lateral width in a range of about 10μ to about 100μ. In some embodiments, the narrowest region of the conductor can have a lateral width in a range of about 10μ to about 50μ. In some embodiments, the narrowest region of the conductor can have a lateral width in a range of about 10μ to about 30μ. In some embodiments, the narrowest region of the conductor can have a lateral width in a range of about 50μ to about 500μ. In some embodiments, the narrowest region of the conductor can have a lateral width in a range of about 50μ to about 300μ. In some embodiments, the narrowest region of the conductor can have a lateral width in a range of about 50μ to about 200μ. In some embodiments, the narrowest region of the conductor can have a lateral width in a range of about 10μ to about 150μ. In some embodiments, the narrowest region of the conductor can have a lateral width in a range of about 50μ to about 100μ. In some embodiments, the narrowest region of the conductor can have a lateral width in a range of about 100μ to about 500μ. In some embodiments, the narrowest region of the conductor can have a lateral width larger than 100μ. In some embodiments, the narrowest region of the conductor can have a lateral width of larger than 150μ. In some embodiments, the narrowest region of the conductor can have a lateral width of larger than 200μ.

The lateral dimension of the narrowest portion of interior of the constricted slot may vary depending on the size of the desired sample or the desired sensitivity. In some embodiments, the constricted slot can have a lateral width in a range of about 1μ to about 1000μ. In some embodiments, the narrowest region of the constricted slot can have a lateral width in a range of about 1μ to about 500μ. In some embodiments, the narrowest region of the constricted slot can have a lateral width in a range of about 1μ to about 300μ. In some embodiments, the narrowest region of the constricted slot can have a lateral width in a range of about 1μ to about 200μ. In some embodiments, the narrowest region of the constricted slot can have a lateral width in a range of about 1μ to about 150μ. In some embodiments, the narrowest region of the constricted slot can have a lateral width in a range of about 1μ to about 120μ. In some embodiments, the narrowest region of the constricted slot can have a lateral width in a range of about 1μ to about 100μ. In some embodiments, the narrowest region of the constricted slot can have a lateral width in a range of about 1μ to about 80μ. In some embodiments, the narrowest region of the constricted slot can have a lateral width in a range of about 1μ to about 50μ. In some embodiments, the narrowest region of the constricted slot can have a lateral width in a range of about 1μ to about 30μ. In some embodiments, the narrowest region of the constricted slot can have a lateral width in a range of about 1μ to about 20μ. In some embodiments, the narrowest region of the constricted slot can have a lateral width in a range of about 1μ to about 10μ. In some embodiments, the constricted slot can have a lateral width in a range of about 10μ to about 1000μ. In some embodiments, the narrowest region of the constricted slot can have a lateral width in a range of about 10μ to about 500μ. In some embodiments, the narrowest region of the constricted slot can have a lateral width in a range of about 10μ to about 300μ. In some embodiments, the narrowest region of the constricted slot can have a lateral width in a range of about 10μ to about 200μ. In some embodiments, the narrowest region of the constricted slot can have a lateral width in a range of about 10μ to about 150μ. In some embodiments, the narrowest region of the constricted slot can have a lateral width in a range of about 10μ to about 120μ. In some embodiments, the narrowest region of the constricted slot can have a lateral width in a range of about 10μ to about 100μ. In some embodiments, the narrowest region of the constricted slot can have a lateral width in a range of about 10μ to about 80μ. In some embodiments, the narrowest region of the constricted slot can have a lateral width in a range of about 10μ to about 50μ. In some embodiments, the narrowest region of the constricted slot can have a lateral width in a range of about 10μ to about 30μ. In some embodiments, the narrowest region of the constricted slot can have a lateral width in a range of about 50μ to about 500μ. In some embodiments, the narrowest region of the constricted slot can have a lateral width in a range of about 50μ to about 300μ. In some embodiments, the narrowest region of the constricted slot can have a lateral width in a range of about 50μ to about 200μ. In some embodiments, the narrowest region of the constricted slot can have a lateral width in a range of about 50μ to about 100μ. In some embodiments, the narrowest region of the constricted slot can have a lateral width in a range of about 50μ to about 120μ. In some embodiments, the narrowest region of the constricted slot can have a lateral width of less than 100μ. In some embodiments, the narrowest region of the constricted slot can have a lateral width of less than 150μ. In some embodiments, the narrowest region of the constricted slot can have a lateral width of less than 120μ. In some embodiments, the narrowest region of the constricted slot can have a lateral width of less than 200μ.

The longitudinal dimension of the constricted slot may vary depending on the size of the desired sample or the desired sensitivity. In some embodiments, the constricted slot can have a length in a range of about 1μ to about 1000μ. In some embodiments, the constricted slot can have a length in a range of about 1μ to about 500μ. In some embodiments, the constricted slot can have a length in a range of about 1μ to about 300μ. In some embodiments, the constricted slot can have a length in a range of about 1μ to about 200μ. In some embodiments, the constricted slot can have a length in a range of about 1μ to about 150μ. In some embodiments, the constricted slot can have a length in a range of about 1μ to about 120μ. In some embodiments, the constricted slot can have a length in a range of about 1μ to about 100μ. In some embodiments, the constricted slot can have a length in a range of about 1μ to about 80μ. In some embodiments, the constricted slot can have a length in a range of about 1μ to about 50μ. In some embodiments, the constricted slot can have a length in a range of about 1μ to about 30μ. In some embodiments, the constricted slot can have a length in a range of about 1μ to about 20μ. In some embodiments, the constricted slot can have a length in a range of about 1μ to about 10μ. In some embodiments, the constricted slot can have a length in a range of about 10μ to about 1000μ. In some embodiments, the constricted slot can have a length in a range of about 10μ to about 500μ. In some embodiments, the constricted slot can have a length in a range of about 10μ to about 300μ. In some embodiments, the constricted slot can have a length in a range of about 10μ to about 200μ. In some embodiments, the constricted slot can have a length in a range of about 10μ to about 150μ. In some embodiments, the constricted slot can have a length in a range of about 10μ to about 120μ. In some embodiments, the constricted slot can have a length in a range of about 10μ to about 100μ. In some embodiments, the constricted slot can have a length in a range of about 10μ to about 80μ. In some embodiments, the constricted slot can have a length in a range of about 10μ to about 50μ. In some embodiments, the constricted slot can have a length in a range of about 10μ to about 30μ. In some embodiments, the constricted slot can have a length in a range of about 50μ to about 500μ. In some embodiments, the constricted slot can have a length in a range of about 50μ to about 300μ. In some embodiments, the constricted slot can have a length in a range of about 50μ to about 200μ. In some embodiments, the constricted slot can have a length in a range of about 50μ to about 100μ. In some embodiments, the constricted slot can have a length in a range of about 50μ to about 120μ. In some embodiments, the constricted slot can have a length of less than 100μ. In some embodiments, the constricted slot can have a length of less than 150μ. In some embodiments, the constricted slot can have a length of less than 120μ. In some embodiments, the constricted slot can have a length of less than 200μ.

As described above, the conductor can have one or more narrowed regions arranged in cascade and the lateral dimension of each narrowed region becomes smaller as the order of the narrowed region becomes higher. In some embodiments, the lateral width of the conductor can be decreased by from about 1% to about 99% at each narrowing as the order increases by one. In some embodiments, the lateral width of the conductor can be decreased by from about 1% to about 90% at each narrowing as the order increases by one. In some embodiments, the lateral width of the conductor can be decreased by from about 1% to about 80% at each narrowing as the order increases by one. In some embodiments, the lateral width of the conductor can be decreased by from about 1% to about 60% at each narrowing as the order increases by one. In some embodiments, the lateral width of the conductor can be decreased by from about 1% to about 50% at each narrowing as the order increases by one. In some embodiments, the lateral width of the conductor can be decreased by from about 1% to about 30% at each narrowing as the order increases by one. In some embodiments, the lateral width of the conductor can be decreased by from about 1% to about 10% at each narrowing as the order increases by one. In some embodiments, the lateral width of the conductor can be decreased by from about 5% to about 80% at each narrowing as the order increases by one. In some embodiments, the lateral width of the conductor can be decreased by from about 5% to about 60% at each narrowing as the order increases by one. In some embodiments, the lateral width of the conductor can be decreased by from about 5% to about 50% at each narrowing as the order increases by one. In some embodiments, the lateral width of the conductor can be decreased by from about 5% to about 30% at each narrowing as the order increases by one. In some embodiments, the lateral width of the conductor can be decreased by from about 10% to about 90% at each narrowing as the order increases by one. In some embodiments, the lateral width of the conductor can be decreased by from about 10% to about 80% at each narrowing as the order increases by one. In some embodiments, the lateral width of the conductor can be decreased by from about 10% to about 60% at each narrowing as the order increases by one. In some embodiments, the lateral width of the conductor can be decreased by from about 10% to about 50% at each narrowing as the order increases by one. In some embodiments, the lateral width of the conductor can be decreased by from about 10% to about 30% at each narrowing as the order increases by one. In some embodiments, the lateral width of the conductor can be decreased by from about 20% to about 90% at each narrowing as the order increases by one. In some embodiments, the lateral width of the conductor can be decreased by from about 20% to about 80% at each narrowing as the order increases by one. In some embodiments, the lateral width of the conductor can be decreased by from about 20% to about 60% at each narrowing as the order increases by one. In some embodiments, the lateral width of the conductor can be decreased by from about 20% to about 40% at each narrowing as the order increases by one. In some embodiments, the lateral width of the conductor can be decreased by from about 30% to about 90% at each narrowing as the order increases by one. In some embodiments, the lateral width of the conductor can be decreased by from about 30% to about 80% at each narrowing as the order increases by one. In some embodiments, the lateral width of the conductor can be decreased by from about 30% to about 60% at each narrowing as the order increases by one. In some embodiments, the lateral width of the conductor can be decreased by from about 50% to about 99% at each narrowing as the order increases by one. In some embodiments, the lateral width of the conductor can be decreased by from about 50% to about 90% at each narrowing as the order increases by one. In some embodiments, the lateral width of the conductor can be decreased by from about 50% to about 80% at each narrowing as the order increases by one. In some embodiments, the lateral width of the conductor can be decreased by from about 50% to about 70% at each narrowing as the order increases by one. In some embodiments, the lateral width of the conductor can be decreased by from about 60% to about 99% at each narrowing as the order increases by one. In some embodiments, the lateral width of the conductor can be decreased by from about 60% to about 90% at each narrowing as the order increases by one. In some embodiments, the lateral width of the conductor can be decreased by from about 60% to about 80% at each narrowing as the order increases by one. In some embodiments, the lateral width of the conductor can be decreased by from about 70% to about 99% at each narrowing as the order increases by one. In some embodiments, the lateral width of the conductor can be decreased by from about 70% to about 90% at each narrowing as the order increases by one. In some embodiments, the lateral width of the conductor can be decreased by from about 80% to about 99% at each narrowing as the order increases by one. In some embodiments, the lateral width of the conductor can be decreased by from about 80% to about 99% at each narrowing as the order increases by one. In some embodiments, the lateral width of the conductor can be decreased by from about 90% to about 99% at each narrowing as the order increases by one. In some embodiments, the lateral width of the conductor can be decreased by no less than 80% at each narrowing as the order increases by one. In some embodiments, the lateral width of the conductor can be decreased by no less than 60% at each narrowing as the order increases by one. In some embodiments, the lateral width of the conductor can be decreased by no less than 50% at each narrowing as the order increases by one. In some embodiments, the lateral width of the conductor can be decreased by no more than 99% at each narrowing as the order increases by one.

As described above in FIGS. 4A through 4D, the first and second wires of the constricted slot can have one or more cascaded outer trimmings as the order of the constricted slot becomes higher. In some embodiments, the lateral width of the wire can be decreased by from about 1% to about 99% at each trimming. In some embodiments, the lateral width of the wire can be decreased by from about 1% to about 90% at each trimming. In some embodiments, the lateral width of the wire can be decreased by from about 1% to about 80% at each trimming. In some embodiments, the lateral width of the wire can be decreased by from about 1% to about 60% at each trimming. In some embodiments, the lateral width of the wire can be decreased by from about 1% to about 50% at each trimming. In some embodiments, the lateral width of the wire can be decreased by from about 1% to about 30% at each trimming. In some embodiments, the lateral width of the wire can be decreased by from about 1% to about 10% at each trimming. In some embodiments, the lateral width of the wire can be decreased by from about 5% to about 80% at each trimming. In some embodiments, the lateral width of the wire can be decreased by from about 5% to about 60% at each trimming. In some embodiments, the lateral width of the wire can be decreased by from about 5% to about 50% at each trimming. In some embodiments, the lateral width of the wire can be decreased by from about 5% to about 30% at each trimming. In some embodiments, the lateral width of the wire can be decreased by from about 10% to about 90% at each trimming. In some embodiments, the lateral width of the wire can be decreased by from about 10% to about 80% at each trimming. In some embodiments, the lateral width of the wire can be decreased by from about 10% to about 60% at each trimming. In some embodiments, the lateral width of the wire can be decreased by from about 10% to about 50% at each trimming. In some embodiments, the lateral width of the wire can be decreased by from about 10% to about 30% at each trimming. In some embodiments, the lateral width of the wire can be decreased by from about 20% to about 90% at each trimming. In some embodiments, the lateral width of the wire can be decreased by from about 20% to about 80% at each trimming. In some embodiments, the lateral width of the wire can be decreased by from about 20% to about 60% at each trimming. In some embodiments, the lateral width of the wire can be decreased by from about 20% to about 40% at each trimming. In some embodiments, the lateral width of the wire can be decreased by from about 30% to about 90% at each trimming. In some embodiments, the lateral width of the wire can be decreased by from about 30% to about 80% at each trimming. In some embodiments, the lateral width of the wire can be decreased by from about 30% to about 60% at each trimming. In some embodiments, the lateral width of the wire can be decreased by from about 50% to about 99% at each trimming. In some embodiments, the lateral width of the wire can be decreased by from about 50% to about 90% at each trimming. In some embodiments, the lateral width of the wire can be decreased by from about 50% to about 80% at each trimming. In some embodiments, the lateral width of the wire can be decreased by from about 50% to about 70% at each trimming. In some embodiments, the lateral width of the wire can be decreased by from about 60% to about 99% at each trimming. In some embodiments, the lateral width of the wire can be decreased by from about 60% to about 90% at each trimming. In some embodiments, the lateral width of the wire can be decreased by from about 60% to about 80% at each trimming. In some embodiments, the lateral width of the wire can be decreased by from about 70% to about 99% at each trimming. In some embodiments, the lateral width of the wire can be decreased by from about 70% to about 90% at each trimming. In some embodiments, the lateral width of the wire can be decreased by from about 80% to about 99% at each trimming. In some embodiments, the lateral width of the wire can be decreased by from about 80% to about 99% at each trimming. In some embodiments, the lateral width of the wire can be decreased by from about 90% to about 99% at each trimming. In some embodiments, the lateral width of the wire can be decreased by no less than 80% at each trimming. In some embodiments, the lateral width of the wire can be decreased by no less than 60% at each trimming. In some embodiments, the lateral width of the wire can be decreased by no less than 50% at each trimming. In some embodiments, the lateral width of the wire can be decreased by no more than 99% at each trimming. In some embodiments, the lateral width of the wire can be decreased by no more than 80% at each trimming. In some embodiments, the lateral width of the wire can be decreased by no more than 60% at each trimming. In some embodiments, the lateral width of the wire can be decreased by no more than 50% at each trimming.

As described above in FIGS. 5A through 5D, the first and second wires forming the edges of the constricted slot can have one or more cascaded intrusions into the slot as the order of the constricted slot becomes higher. The lateral width of the wire may remain the same after being trimmed from the side facing away from the aperture due to the intrusions from the side facing the aperture. Alternatively, the lateral width of the wire may increase along the cascaded intrusions. In some embodiments, the lateral width of the wire can be increased by from about 1% to about 100% after one intrusion being added. In some embodiments, the lateral width of the wire can be increased by from about 1% to about 90% after one intrusion being added. In some embodiments, the lateral width of the wire can be increased by from about 1% to about 80% after one intrusion being added. In some embodiments, the lateral width of the wire can be increased by from about 1% to about 60% after one intrusion being added. In some embodiments, the lateral width of the wire can be increased by from about 1% to about 50% after one intrusion being added. In some embodiments, the lateral width of the wire can be increased by from about 1% to about 30% after one intrusion being added. In some embodiments, the lateral width of the wire can be increased by from about 1% to about 10% after one intrusion being added. In some embodiments, the lateral width of the wire can be increased by from about 5% to about 80% after one intrusion being added. In some embodiments, the lateral width of the wire can be increased by from about 5% to about 60% after one intrusion being added. In some embodiments, the lateral width of the wire can be increased by from about 5% to about 50% after one intrusion being added. In some embodiments, the lateral width of the wire can be increased by from about 5% to about 30% after one intrusion being added. In some embodiments, the lateral width of the wire can be increased by from about 10% to about 90% after one intrusion being added. In some embodiments, the lateral width of the wire can be increased by from about 10% to about 80% after one intrusion being added. In some embodiments, the lateral width of the wire can be increased by from about 10% to about 60% after one intrusion being added. In some embodiments, the lateral width of the wire can be increased by from about 10% to about 50% after one intrusion being added. In some embodiments, the lateral width of the wire can be increased by from about 10% to about 30% after one intrusion being added. In some embodiments, the lateral width of the wire can be increased by from about 20% to about 90% after one intrusion being added. In some embodiments, the lateral width of the wire can be increased by from about 20% to about 80% after one intrusion being added. In some embodiments, the lateral width of the wire can be increased by from about 20% to about 60% after one intrusion being added. In some embodiments, the lateral width of the wire can be increased by from about 20% to about 40% after one intrusion being added. In some embodiments, the lateral width of the wire can be increased by from about 30% to about 90% after one intrusion being added. In some embodiments, the lateral width of the wire can be increased by from about 30% to about 80% after one intrusion being added. In some embodiments, the lateral width of the wire can be increased by from about 30% to about 60% after one intrusion being added. In some embodiments, the lateral width of the wire can be increased by from about 50% to about 99% after one intrusion being added. In some embodiments, the lateral width of the wire can be increased by from about 50% to about 90% after one intrusion being added. In some embodiments, the lateral width of the wire can be increased by from about 50% to about 80% after one intrusion being added. In some embodiments, the lateral width of the wire can be increased by from about 50% to about 70% after one intrusion being added. In some embodiments, the lateral width of the wire can be increased by from about 60% to about 99% after one intrusion being added. In some embodiments, the lateral width of the wire can be increased by from about 60% to about 90% after one intrusion being added. In some embodiments, the lateral width of the wire can be increased by from about 60% to about 80% after one intrusion being added. In some embodiments, the lateral width of the wire can be increased by from about 70% to about 99% after one intrusion being added. In some embodiments, the lateral width of the wire can be increased by from about 70% to about 90% after one intrusion being added. In some embodiments, the lateral width of the wire can be increased by from about 80% to about 99% after one intrusion being added. In some embodiments, the lateral width of the wire can be increased by from about 80% to about 100% after one intrusion being added. In some embodiments, the lateral width of the wire can be increased by from about 90% to about 100% after one intrusion being added. In some embodiments, the lateral width of the wire can be increased by no less than 80% after one intrusion being added. In some embodiments, the lateral width of the wire can be increased by no less than 60% after one intrusion being added. In some embodiments, the lateral width of the wire can be increased by no less than 50% after one intrusion being added. In some embodiments, the lateral width of the wire can be increased by no more than 99% after one intrusion being added. In some embodiments, the lateral width of the wire can be increased by no more than 80% after one intrusion being added. In some embodiments, the lateral width of the wire can be increased by no more than 60% after one intrusion being added. In some embodiments, the lateral width of the wire can be increased by no more than 50% after one intrusion being added.

Figure 7A:
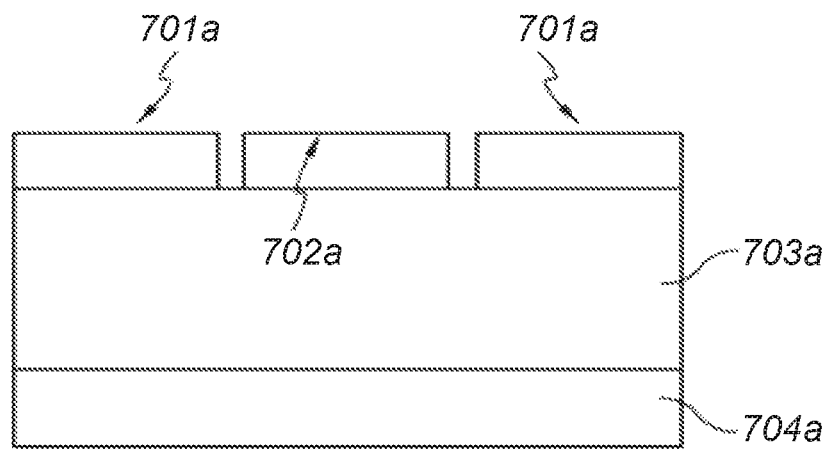
FIGS. 7A and 7B show examples of probe configurations. (7A) Grounded coplanar waveguide (GCPW) configuration. (7B) Regular coplanar waveguide (CPW) configuration.
Figure 7B:
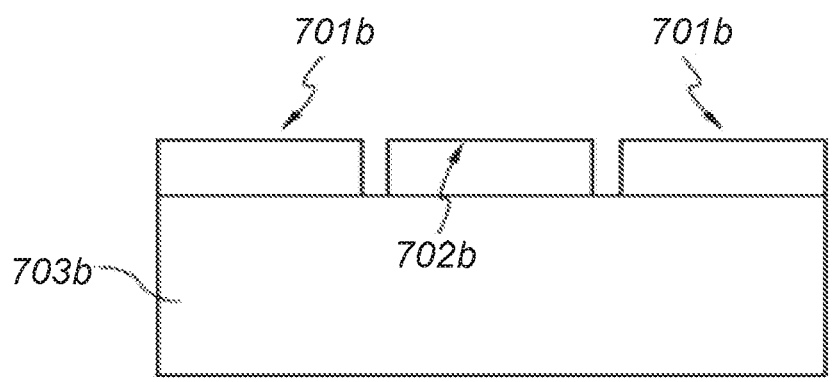

FIGS. 7A and 7B show examples of configurations of a magnetic resonance probe comprising a constricted slot. FIG. 7A is a cross-section of a grounded coplanar waveguide (GCPW) configuration. FIG. 7B is a cross-section of a regular coplanar waveguide (CPW) configuration. As shown in FIGS. 7A and 7B, the constricted slot may be embedded in the conductor of the probe. FIG. 7A shows that the constricted slot can be used in the center conductor (trace or strip) 702a of a grounded coplanar waveguide (GCPW). FIG. 7B shows that the constricted slot can also be used the conductor (trace or strip) 702b of the coplanar waveguide (CPW). The coplanar waveguide is feasible for measuring conductive samples or for probing film samples. As shown in FIG. 7A, the GCPW configuration includes a conductor (trace or strip) 702a, a substrate 703a, a coplanar waveguide grounding plate 701a, and a grounding plate 704a. The substrate 703a is positioned between a coplanar waveguide grounding plate 701a and a bottom grounding plate 704a. The configuration shown in FIG. 7B includes a conductor (trace or strip) 702b, a substrate 703b, and a coplanar waveguide grounding plate 701b. In some applications (such as in measurements of hard matter, thin films and more conductive samples) the coplanar waveguide may be preferable, whereas in other applications (such as measurements of soft matter samples) the GCPW configuration may be preferred.

Figure 8A:
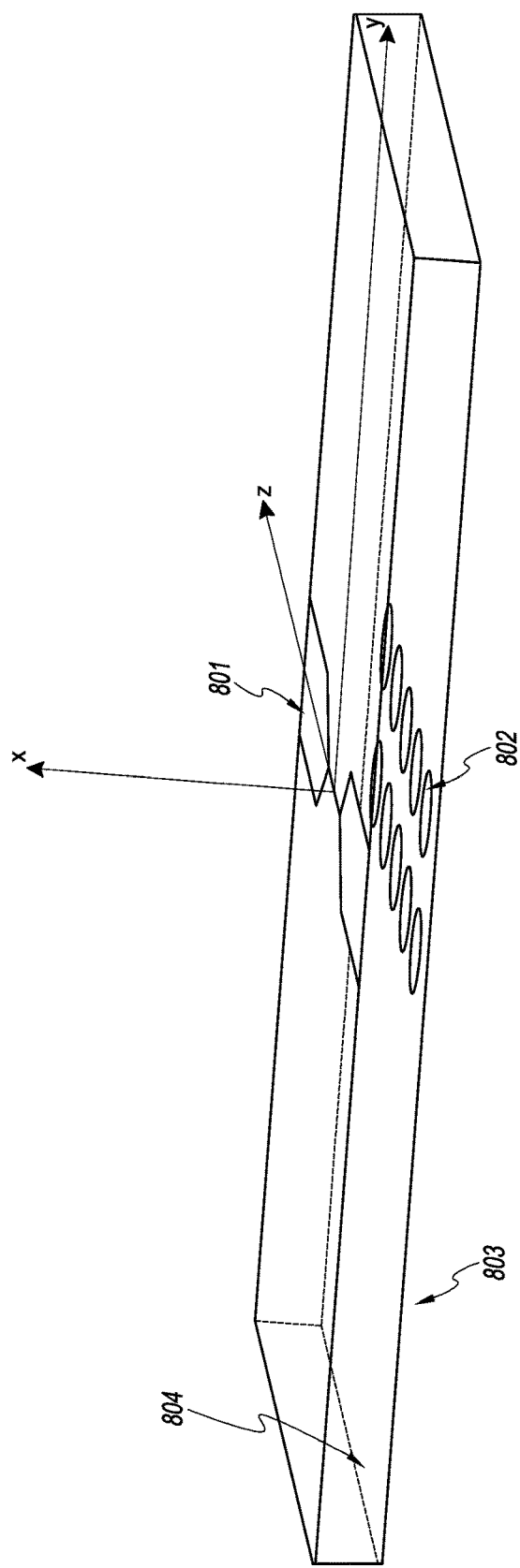
FIGS. 8A and 8B illustrate an example of the noise mitigation mechanism. (8A) Noise mitigation mechanism used in the microstrip. Noise mitigation is achieved by perforating the ground plane below the microstrip. (8B) Noise mitigation mechanism used in the coplanar waveguide. Reduction of Johnson noise is accomplished through the removal of unnecessary metal.
Figure 8B:
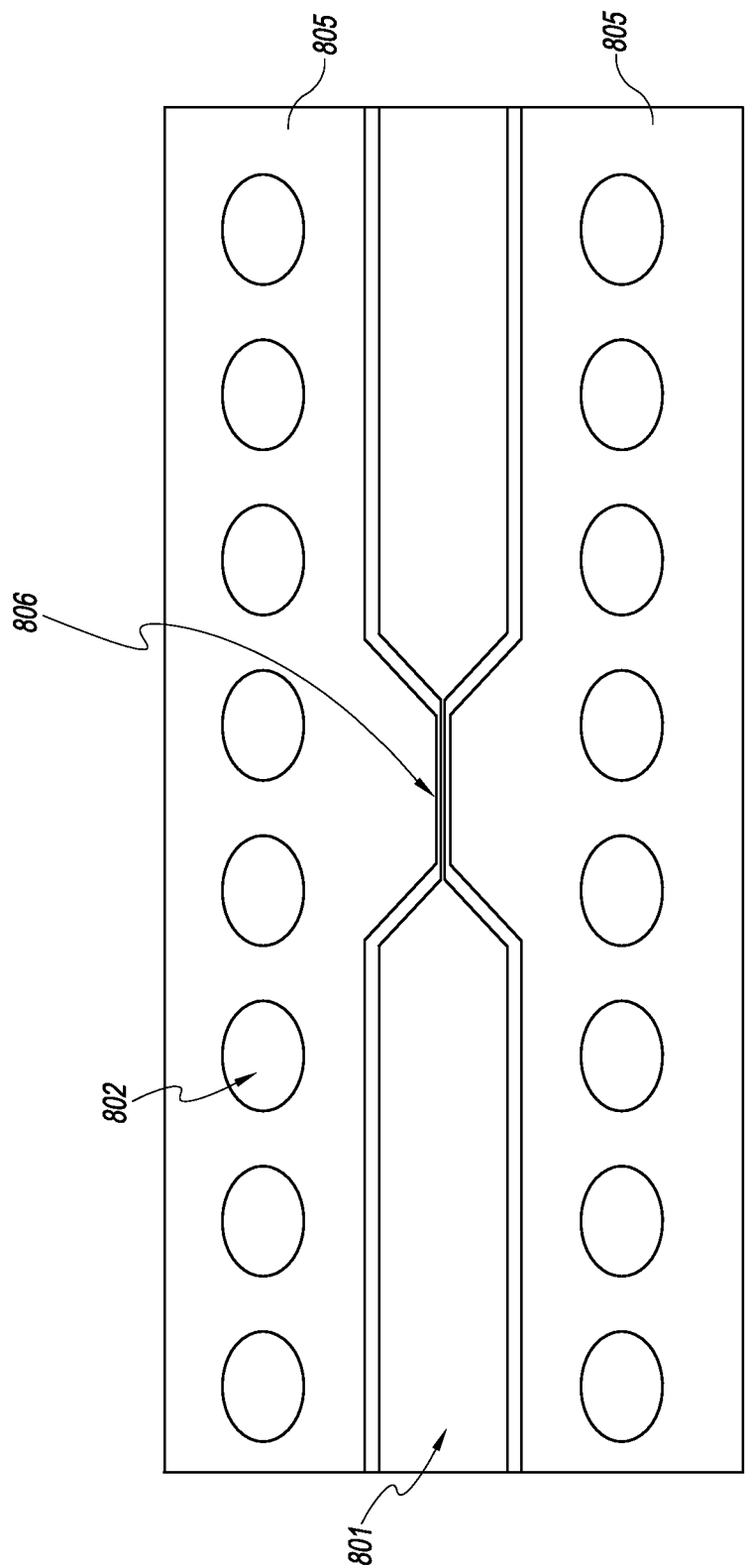

FIGS. 8A and 8B illustrate examples of a noise mitigation mechanism. In FIG. 8A, a plurality of perforations 802 are cut through the ground plate 803 (e.g., by machining or laser or chemical etching). The perforations 802 are preferably close to the conductor 801 but not beneath it. The conductor and the perforations are spaced apart from each other. As shown in FIGS. 8B and 8C, the perforations 802 surround the conductor 801 but do not overlap with the conductor 801 or the constricted slot 806. These perforations can reduce the thermal noise (Johnson noise) picked up by the probe and improve the SNR. The SNR can be improved by 22% when the diameter of the perforation is 5 mm.

Figure 9:
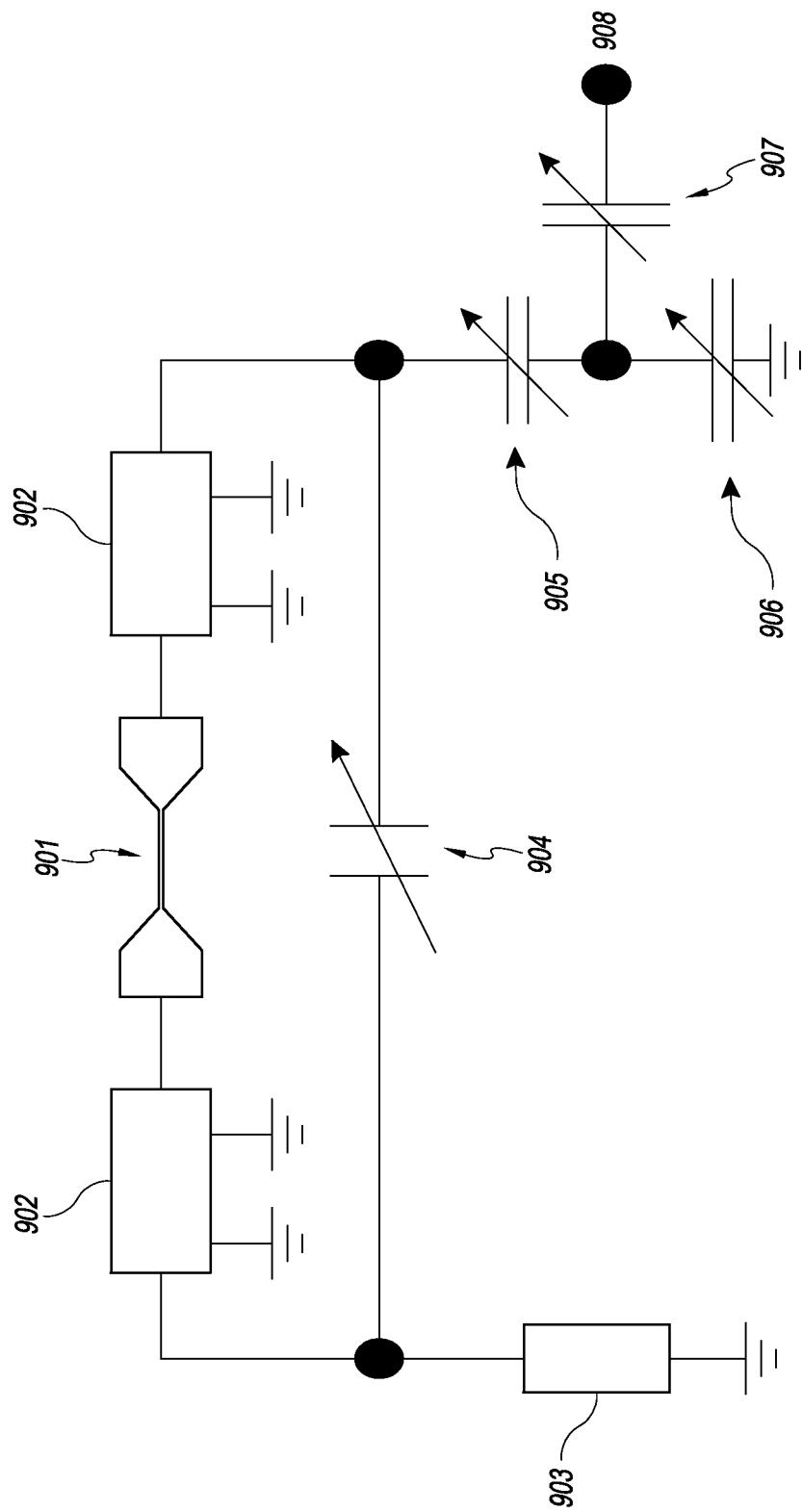
FIG. 9 shows an example of a circuit diagram of a balanced, single resonance (single channel), micro-NMR probe.

FIG. 9 shows a circuit diagram including a balanced, single resonance, micro-magnetic resonance probe as described above. The conductor with a constricted slot can be used in the probe as shown in FIG. 9. The balancing module 903 is a capacitive device such as a variable capacitor used to balance the constricted section 901. The parallel capacitor 904 increases the reactance of the resonance circuit to direct more RF power toward the constricted section 901. The center of the constricted section 901 is the detection region. The extension transmission lines 902 connect the constricted section 901 to the rest of the probe circuit. The impedance adjustment capacitor 905 makes the resonance circuit tunable. The tuning capacitor 906 and matching capacitor 907 are adjusted to make the probe resonate at the working frequency and matched to 50 Ohm at the port 908 respectively. The port 908 can be connected to the duplexer of an NMR console.

In some embodiments, the probe can include a balanced resonator. The RF magnetic field becomes stronger and the common-mode noise pick-up is weakened when the resonator is balanced. The efficiency and SNR of the probe is improved. The balanced resonator also has less heating and becomes less sensitive to the dielectric and conductive properties of samples.

In some embodiments, the probe can include a balanced circuit. A balanced circuit can improve the performance of the magnetic resonance probe. The probe can be balanced either manually or automatically. In some embodiments, the magnetic resonance probe can include an adjustment element to balance the circuit automatically. In some embodiments, both the circuit and the resonator are balanced.

Figure 10:
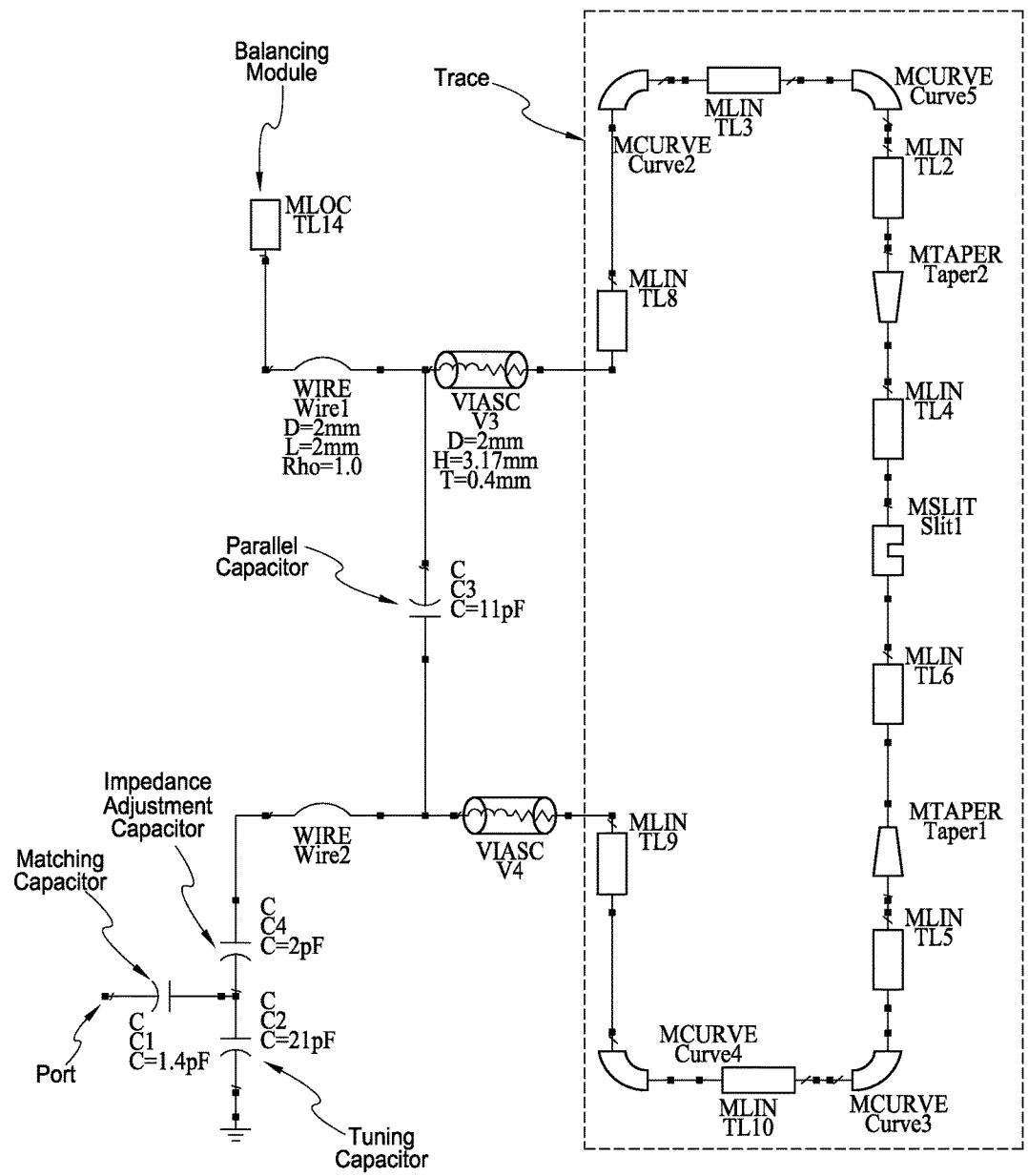
FIG. 10 illustrates an example of the analog model of the circuit of the micro-NMR probe.

FIG. 10 is an analog model of the circuit of a constricted slot based probe. This analogue model can be made by the Advanced Design System (ADS) software or other suitable software. Values of the capacitor and dimensions shown are for one particular embodiment of this invention and are meant to be for illustration purposes only. Actual values in specific implementations of this circuit may vary depending on applications.

Figure 11:
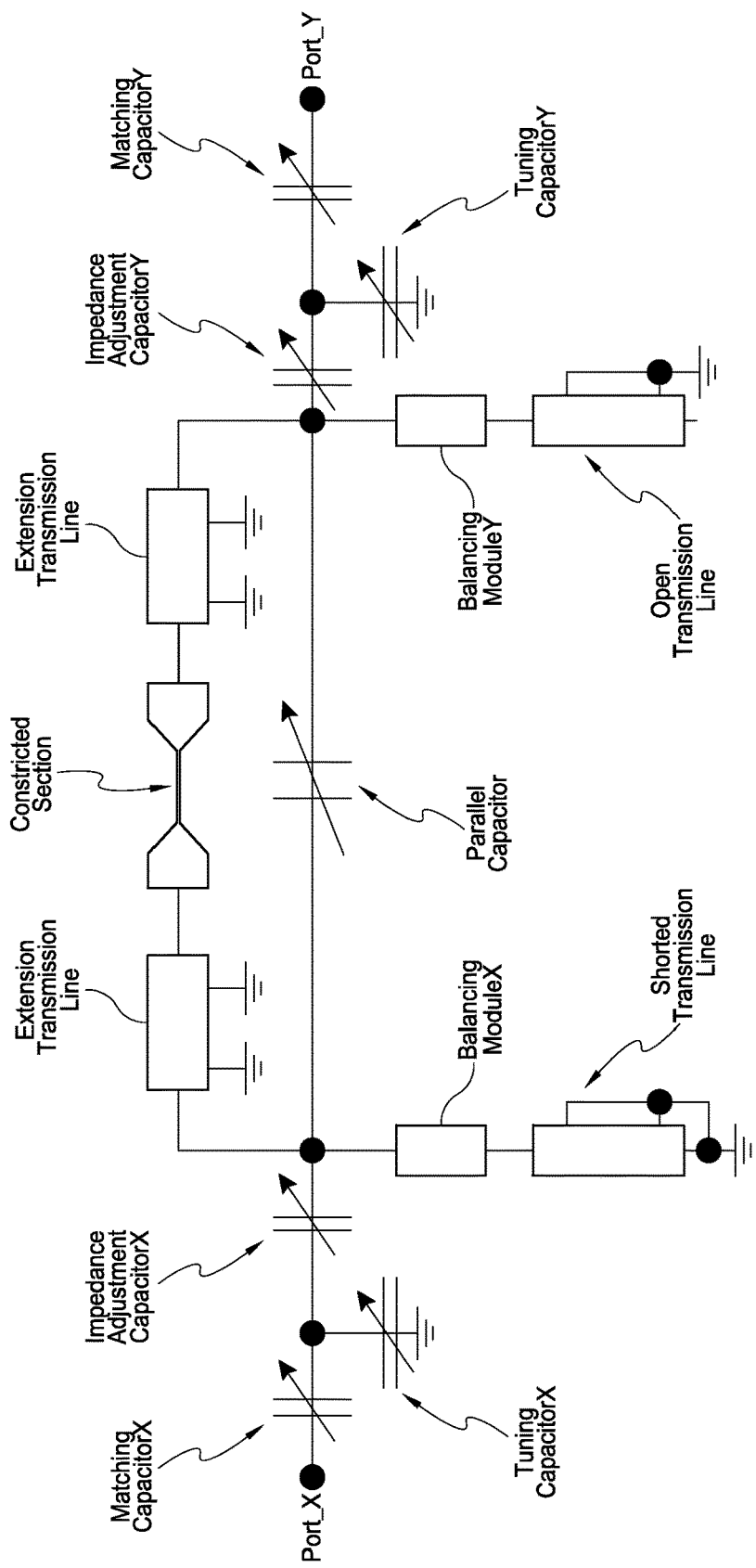
FIG. 11 illustrates an example of the analog model of the circuit of the NMR probe for double resonance (double channel) operation.

The constricted slot-based conductor can also be used in a multiple resonance probe. FIG. 11 shows an example of a double resonance (double channel) operation. The number of resonance may be more than two. The two channels are labeled as port X and port Y. The analog model of the circuit includes X and Y channels. The convention in NMR is that the X nucleus has higher working RF frequency than Y. The shorted transmission line and open transmission line has the length of ¼ wavelength at X frequency. The parallel capacitor increases the reactance of the resonance circuit to direct more RF power toward the constricted section. The conductor and outer conductor at the lower ends of the shorted transmission line and open transmission line are shorted and open respectively. The balancing module X and balancing module Y are capacitive devices at X frequency and Y frequency respectively. The impedance adjustment capacitors are used to tune and match the resonant circuit. The tuning and matching capacitors for each frequency are adjusted to make the NMR probe resonate at each working frequency at that port respectively. The ports are connected to the duplexers of the NMR console.

Figure 12A:
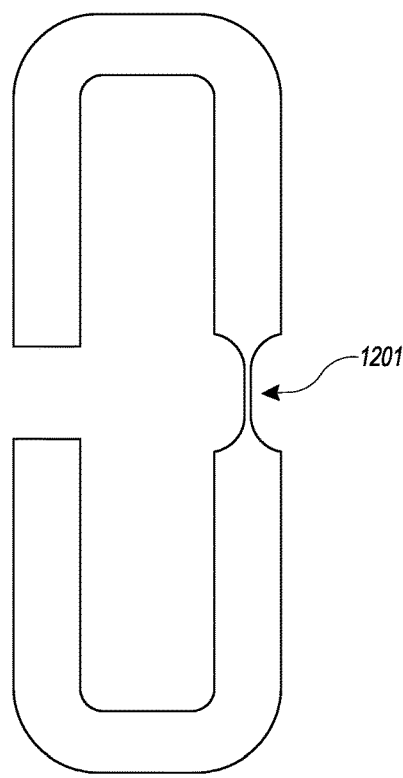
FIGS. 12A through 12D illustrate examples of the single resonance NMR probe laminate (printed circuit board). (12A) The conductor with first constriction. (12B) The constricted slot (at the second constriction). (12C) The top view of the probe circuit. (12D) The rear view (back plane) of the probe circuit.
Figure 12B:
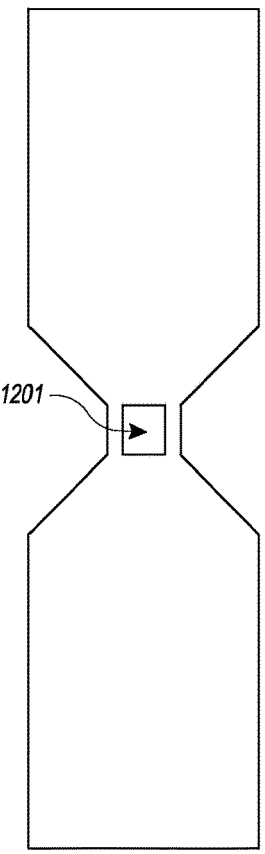
Figure 12C:
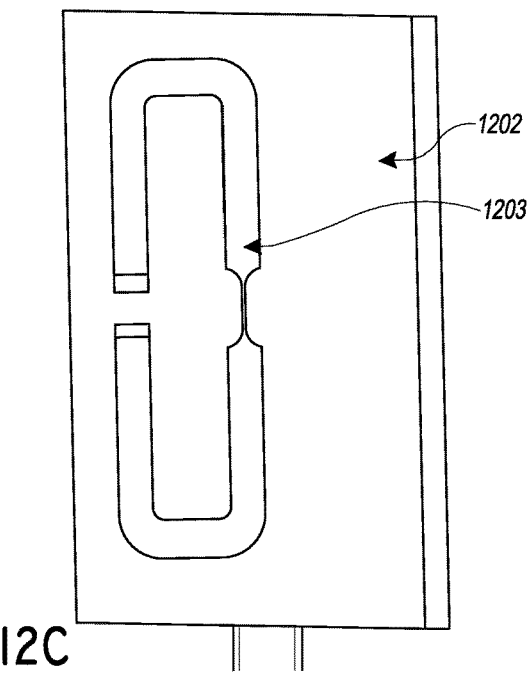
Figure 12D:
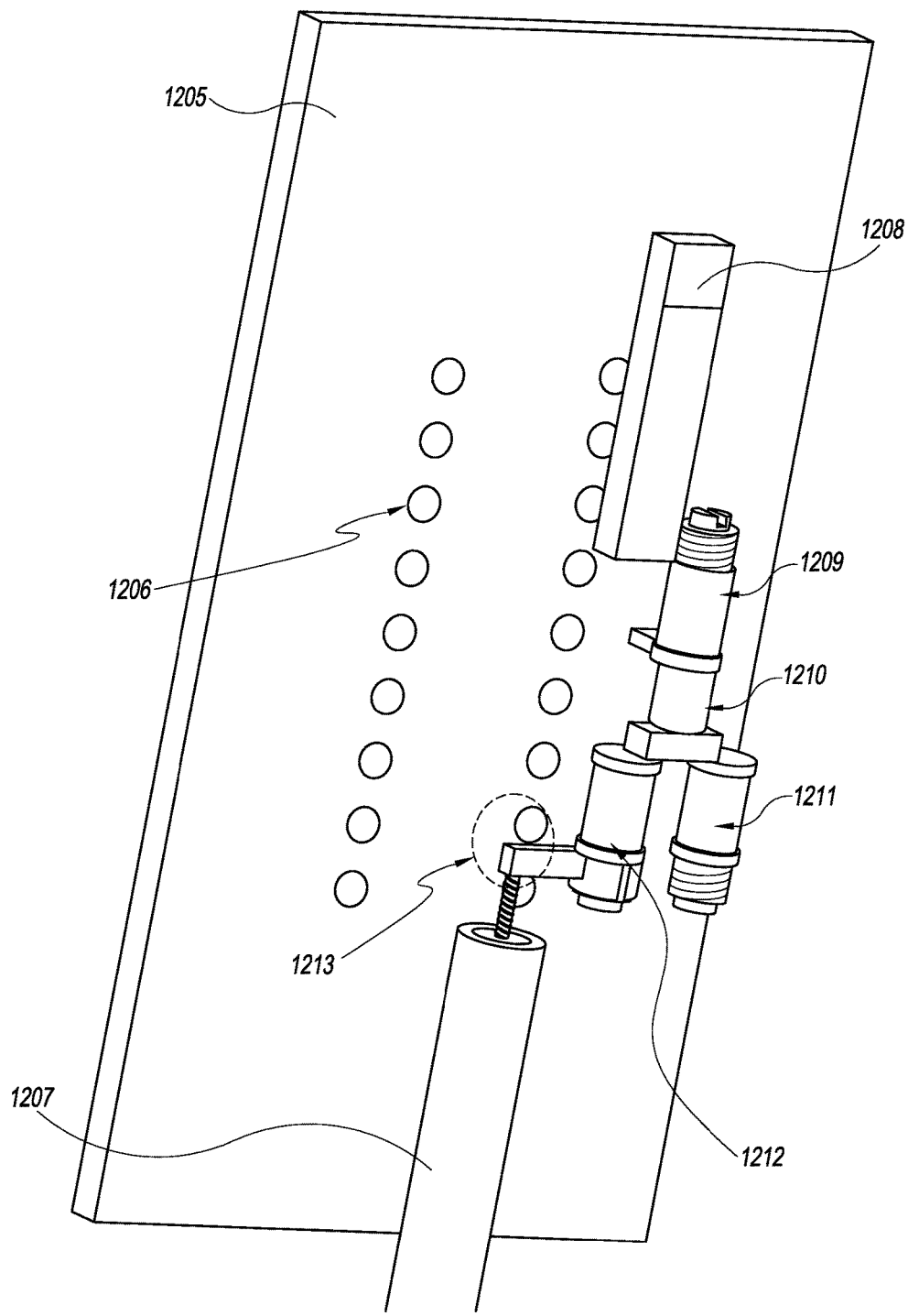

FIGS. 12A through 12D show examples of a single resonance NMR probe laminate (printed circuit board) including the circuit described in FIG. 9. In FIG. 12A, the conductor includes a first constriction. The arrow points to the location of the second constriction, illustrated in greater details in 12B. FIG. 12B is a close-up view showing a second constriction with a constricted slot 1201 in FIG. 12A. The constricted slot based detector can be laminated in the printed circuit board. FIG. 12C shows a front view of the probe circuit, and FIG. 12D shows a rear view of the probe circuit. In FIG. 12C, the conductor 1203 is laminated on the substrate 1202. In FIG. 12D, the balancing module 1208 is a capacitive device such as a variable capacitor used to balance the constricted section. The parallel capacitor 1209 increases the reactance of the resonance circuit to direct more RF power toward the constricted section. The impedance adjustment capacitor 1210 makes the resonance circuit tunable. The tuning capacitor 1211 and matching capacitor 1212 are adjusted to make the NMR probe resonate at the working frequency at the port 1213 respectively. The port 1213 can be connected to a duplexer through the cable 1207. The perforations 1206 in the ground plate 1205 are for Johnson noise mitigation and are optional. The probe shown in FIG. 12D may operate without the perforations.

Figure 13C:
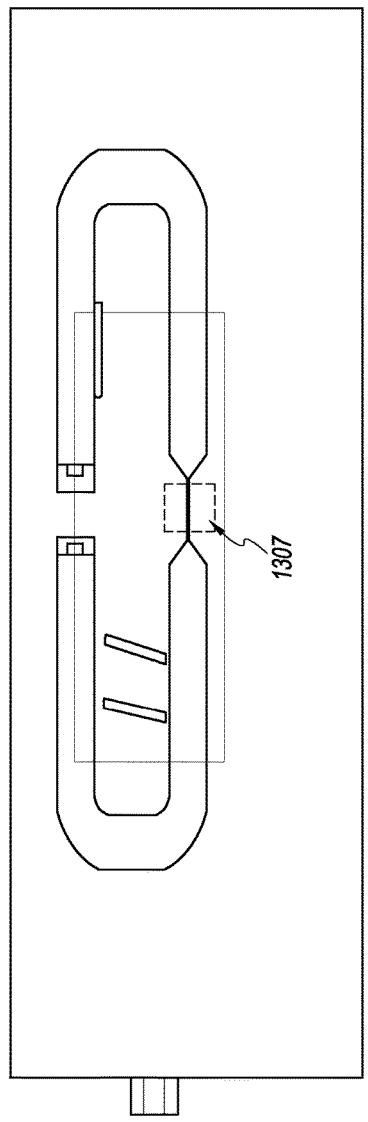
Figure 13D:
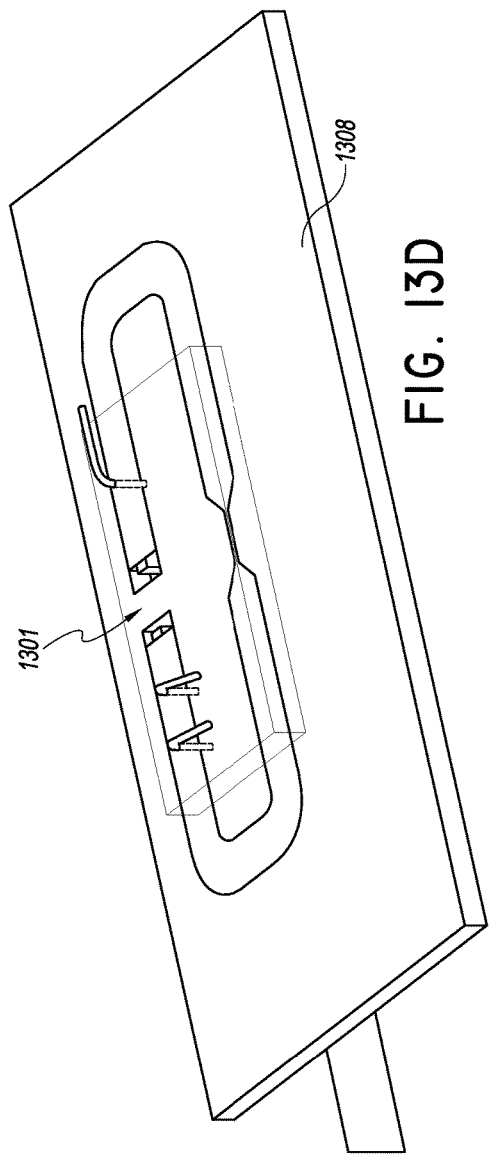

This magnetic resonance probe can be combined with the microfluidic chip to constitute the microfluidic magnetic resonance system. FIGS. 13A through 13D illustrate a single resonance microfluidic magnetic resonance system. FIG. 13A shows an example of a microfluidic chip. The microfluidic ship 1301 includes one or more channels 1302 and one or more tygon tubing providing input and output ports. FIG. 13B (not to scale) shows a detailed cross-section view of the constricted slot region overlaying the microfluidic chip. In FIG. 13B, the conductor 1304 is located on top of the substrate 1305. The microfluidic chip 1301 is placed on top of the conductor 1304 and the channel 1302 of the microfluidic chip can be placed adjacent to and right above the constricted slot of the conductor. The center of the channel is aligned with the center of the constricted slot. The cases of cellular analysis, the cell sample 1306 can be introduced into the channel 1302 and be characterized using the probe. The cell can be manipulated by optical tweezers or any other devices as needed, etc. The tubings shown serve as the inlet and outlet of the microfluidic chip. The tubing can be any suitable flow connector including but not limited to Tygon tubing and any other microfluidic tubing such as PEEK. FIG. 13C is a front view of a magnetic resonance system with a microfluidic chip, and FIG. 13D is a perspective view of the system. The region of interest (channel) in the microfluidic chip 1301 is aligned with the detection region (constricted slot) 1307 of the magnetic resonance probe as shown in FIGS. 13C and 13D.

In some embodiments, the NMR probe can be coupled to a single-channel microfluidic chip. The alignment with the conductor strip comprising the constricted slot can be done manually or automatically. The alignment with the constricted slot may be done manually by microscopic inspection. Optically opaque structures in the channel may be added to help with the alignment. As the sample (e.g., cells) flow into the detector region, the probe tuning may be subject to fluctuations. This can be compensated using automatic tuning and automatic balancing adjustment circuits using varactors. The adjustment can be instantaneous and the probe can always stay tuned during the measurement even when the fluid properties change.

A wide variety of microfluidic device may be coupled to the magnetic resonance probe described herein. For example, the microfluidic devices may be made from PDMS molded microchannels bonded to borosilicate glass coverslips (0.1 mm). The thin glass coverslip allows placement of the RF probe in close proximity to the channels, yielding sensitive measurements of traversing cells. The signal from the PDMS can be minimized to prevent interference with signals of interest by using a spin-echo preparation to use the large difference in $T_2$ times between PDMS and solution samples. In addition, any residual signal overlap can be limited given that the PDMS signal is centered at 0 ppm while choline signals of interest are at 3.2 ppm.

Some embodiments relate to a method of detecting magnetic resonance in a sample. The method includes providing magnetic resonance probe comprising an elongated conductor, wherein the conductor having one or more cascaded narrowed regions along its longitudinal dimension and a slot; positioning the sample inside or adjacent to the slot; applying an electrical excitation signal to energize the conductor; and detecting an electromagnetic signal emanating from the sample.

Some embodiments relate to a method of analyzing a sample. The method includes providing magnetic resonance probe comprising an elongated conductor, wherein the conductor having one or more cascaded narrowed regions along its longitudinal dimension and a slot, and introducing the sample into a microfluidic chip, wherein the microfluidic chip comprises one or more channels configured to transport the sample and is positioned inside or adjacent to the slot; transporting the sample through the channels of the microfluidic chip; applying an electromagnetic excitation signal to energize the conductor; and detecting an electromagnetic signal emanating from the sample.

In some embodiments, the electromagnetic signal emanating from the sample can be used to identify the presence of a cancer cell or any other pathology that may be detected through the NMR signal.

The microfluidic channel through which the sample flows can be placed in the detection region of the conductor. The microfluidic chip may be aligned with the constricted slot so that the microfluidic channel is positioned adjacent to and aligned with the constricted slot. In some embodiments, the microfluidic chip can be aligned with the slot manually or automatically. In some embodiments, the microfluidic chip can be aligned with the slot manually. In some embodiments, the microfluidic chip can be aligned with the slot automatically.

EXAMPLES

Example 1. Conductor with a Constricted Slot

Figure 16A:
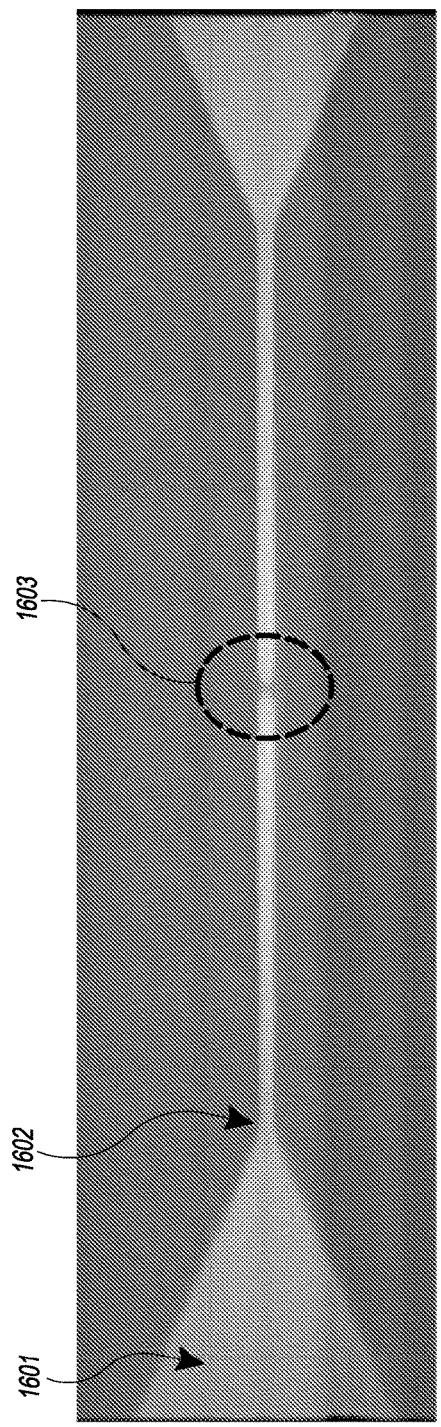
FIGS. 16A and 16B show photographs of a physical realization of the constricted slot.
Figure 16B:
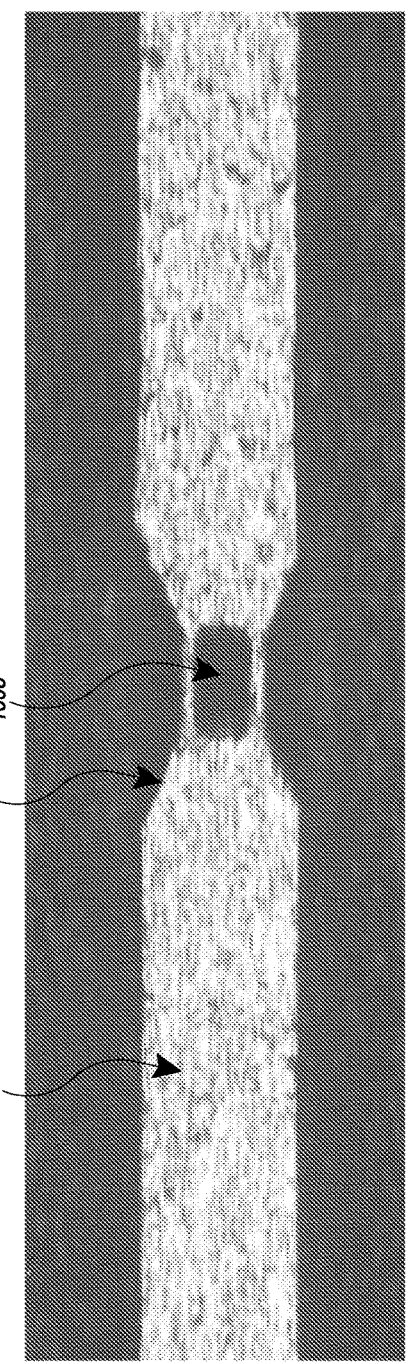

FIGS. 16A and 16B are photographs of a physical realization of the constricted slot which was obtained through laser etching of a copper clad laminate. As shown in FIG. 16A, the conductor 1601 includes a first constriction region 1602 and a constricted slot 1603. FIG. 16B is a close-up view of the constricted slot 1603 shown in FIG. 16A. In FIG. 16B, a second constriction region 1604 is formed in the first constriction region 1602, and the constricted slot 1605 is located within the second constriction region 1604. The center of the constricted slot 1605 overlap with the center of the second constriction region 1604.

Example 2. A Balanced NMR Probe with a Constricted Slot

A balanced 400 MHz $^1$H NMR probe employing an conductor with a constricted slot was designed and constructed. FIG. 14A shows the top view of the RF probe head, illustrating the stripline and its constriction. The front of the high frequency laminate (RT-Duroid5880 from Rogers Corp.) is shown in FIG. 14A. FIG. 14B is a close-up view of the constricted slot 1401. The constricted part of the copper trace is the conductor portion (detection region) of the NMR probe. On the laminate, there is a copper trace (conductor) etched. The trace etching was done via wet etching techniques and the constricted slot was etched via IR laser etching. This side of the laminate is where the NMR conductor (detection region) is located.

Figure 15:
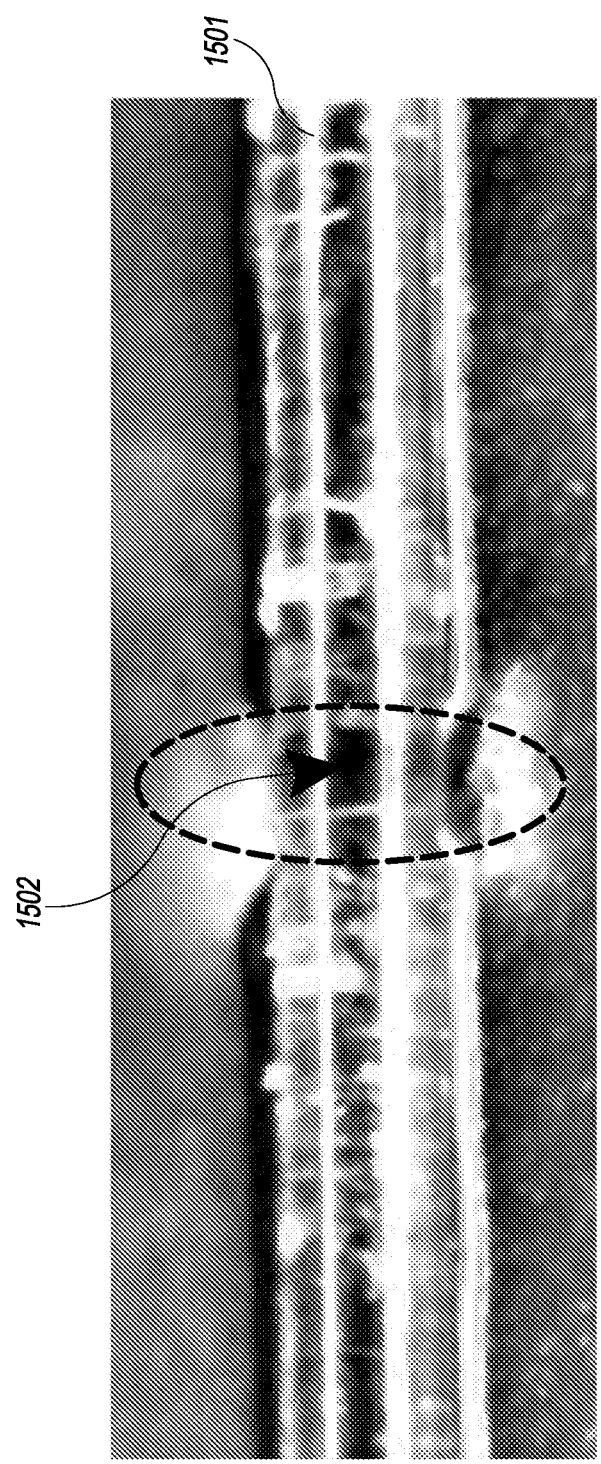
FIG. 15 shows a photograph of a physical realization of the constricted slot aligned with the microfluidic channel.

FIG. 15 is a photograph of a physical realization of the constricted slot aligned with a microfluidic channel. The microfluidic channel shown in FIG. 15 is a simple capillary tube. In FIG. 15, a fluidic capillary tube 1501 filled with liquid sample has been overlaid on top of the detection region 1502 of the NMR probe conductor. The capillary tube 1501 was placed to run parallel to the conductor strip. The constriction slot achieved a significant enhancement in the level of sensitivity. A microfluidic chip can be used instead of a capillary tube, in which case, the fluidic channel must be aligned above the constricted slot.

After etching the conductor, the perforations and the constricted slot were etched on the conductor. The laminate was then mounted onto the NMR probe frame. Then, other circuit components were installed onto this laminate. Fine adjustment was performed until the NMR probe circuit was functional. The back side of the high frequency laminate the balancing module included the noise mitigation mechanism (perforations) implemented via wet etching.

The NMR probe was tested with deionized water in order to determine the limit of detection (LOD) for proton nuclei using a single scan. A capillary with 0.13 mm outer diameter and 0.05 mm inner diameter were mounted onto the detection region.

The NMR probe achieved the following performance: 1) a detection region size of 0.08 mm length by up to 0.05 mm width, 2) LOD of 2.5 pmol spins/square root (Hz) at 600 MHz proton Larmor frequency; and 3) RF power efficiency of 2 watts at 100 kHz proton nutation frequency.

The comparison of the LOD of proton with a single scan when SNR equals to 3 among different detector configurations is shown in Table 1. The LOD of the proton with a single scan from other probes are recalculated from the published papers. The LOD is normalized to 600 MHz for comparison.

TABLE 1

The comparison of the LOD of proton with a single scan among different detector configurations.

| Detector configuration | Effective sample volume (nL) | Distance between sample center and strip (mm) | LOD of proton with a single scan (nmol) | Line-width (Hz) | LOD of proton with a single scan when line width is normalized to 1 Hz (pmol) |
|---|---|---|---|---|---|
| Stripline [1] | 12 | 0.075 | 1.398 | 50 | 28 |
| Microslot [2] | >4.42* | 0.185 | >1.92 | 3.6 | >533 |
| Constricted Slot | 0.157 | 0.065 | 0.183 | 74 | 2.5 |

*The sample length in the microslot NMR probe was larger than 1 mm, according to Reference [2]. In Table 1, the sample length was taken as 1 mm for easy comparison.
References:
[1] van Bentum PJ, Janssen JW, Kentgens AP, Bart J, Gardeniers JG. Stripline probes for nuclear magnetic resonance. J. Magn. Reson. 189:104-113 (2007)
[2] Krojanski HG, Lambert, J, Gerikalan Y, Suter D, Hergenrder, Microslot NMR Probe for Metabolomics Studies, Anal. Chem. 80: 86688672 (2008)

Figure 17A:
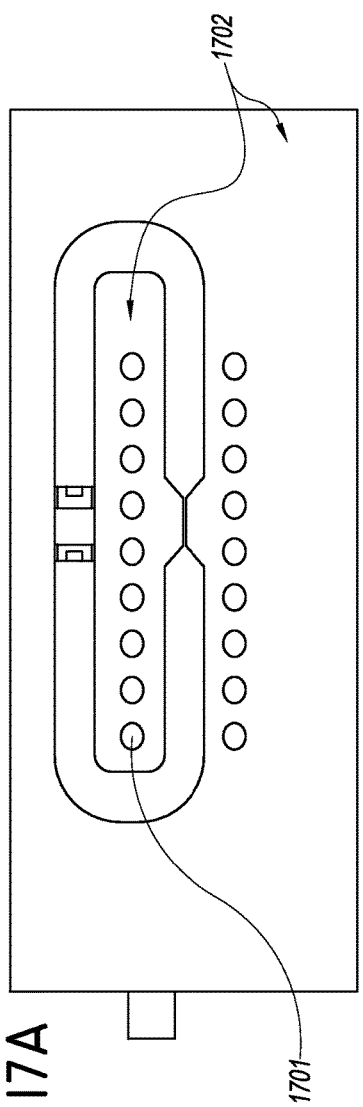
Figure 17B:
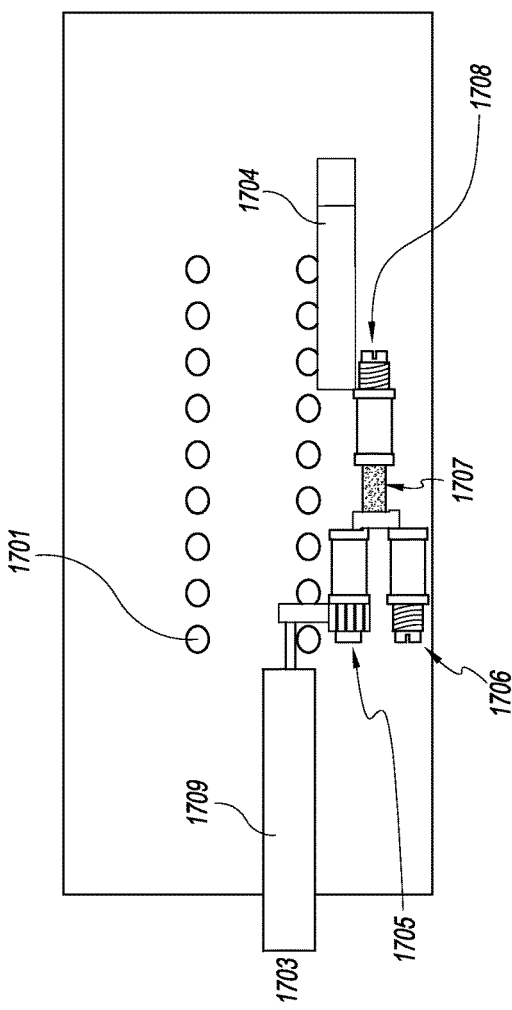

The constricted slot NMR probe has much lower and better LOD of proton than other microstrip NMR probes. The conductor with a constricted slot can also be used in thin film micro-NMR probe. FIGS. 17A through 17C show examples of the laminate of the thin film micro-NMR probe. FIG. 17A is a front view of the laminate. FIG. 17B is a rear view of the laminate. FIG. 17C is a perspective view of the laminate showing the front view, on top of which the position of the ground plate perforations (on the back plane) has been indicated.

The coplanar wave guide was used to confine the $B_1$ field close to the trace and to reduce susceptibility problems. In FIG. 17A, the perforations are formed on the coplanar waveguide grounding plate. This NMR probe can be used to study the properties of thin films, biological samples or fuel cell membranes. In FIG. 17B, the balancing module 1704 is a capacitive device like a variable capacitor used to balance the constricted section. The parallel capacitor 1708 increases the reactance of the resonance circuit to direct more RF power toward the constricted section. The impedance adjustment capacitor 1707 makes the resonance circuit tunable.

The tuning capacitor 1706 and matching capacitor 1705 are adjusted to make the NMR probe resonate at the working frequency and matched to a desired Ohm value at the port 1703 respectively. The port 1703 is connected to the duplexer through the cable 17709.

Figure 18A:
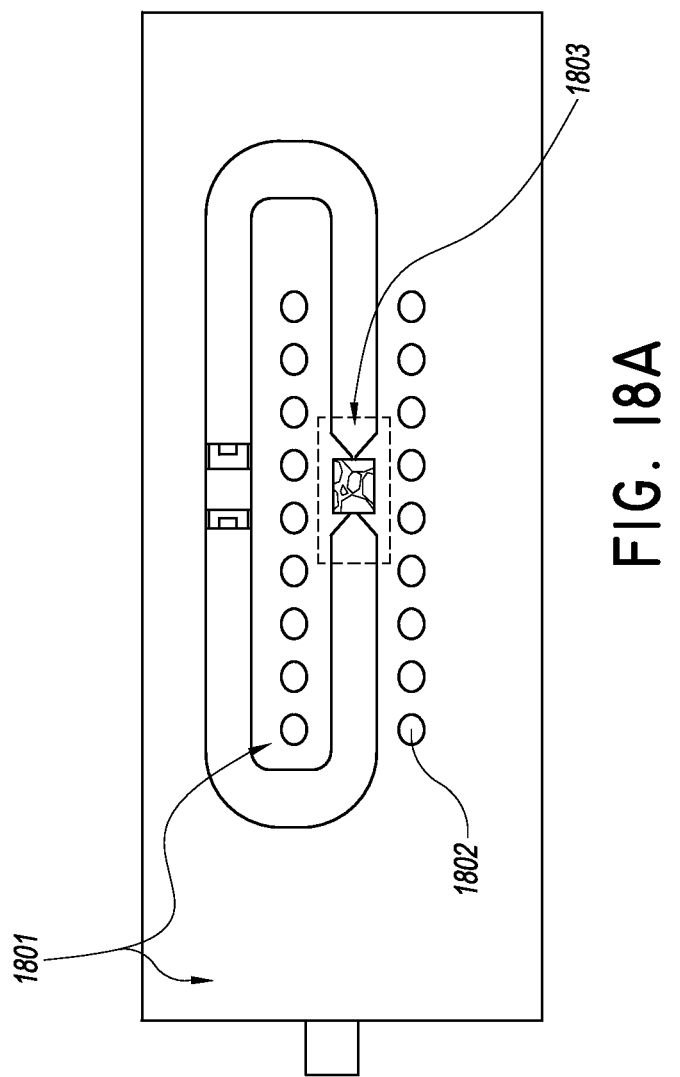
FIGS. 18A through 18C illustrate examples of the thin film NMR probe. (18A) The front view of the probe. (18B) The detailed cross-section view of the constricted section. (18C) Perspective view of the probe.
Figure 18B:
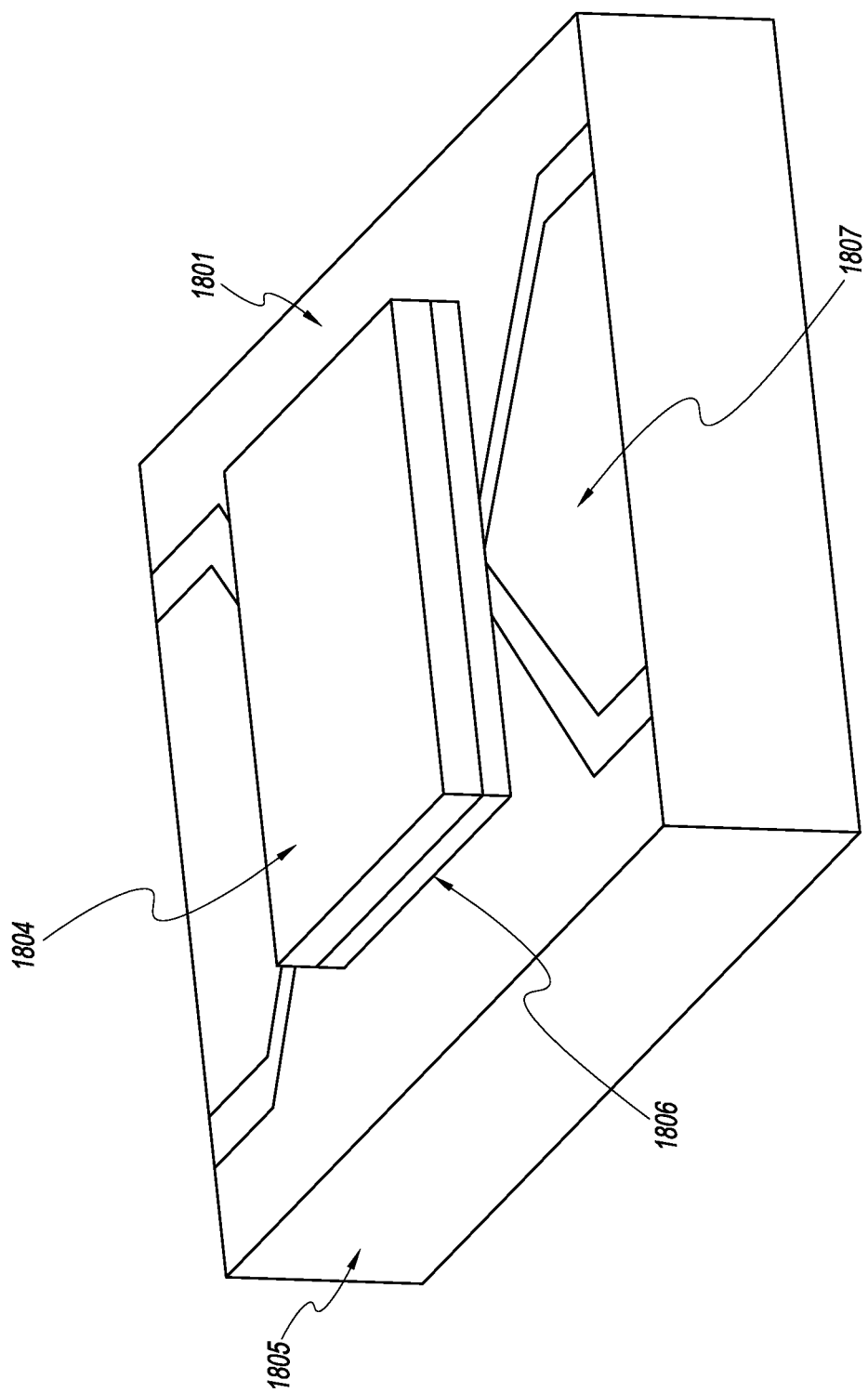
Figure 18C:
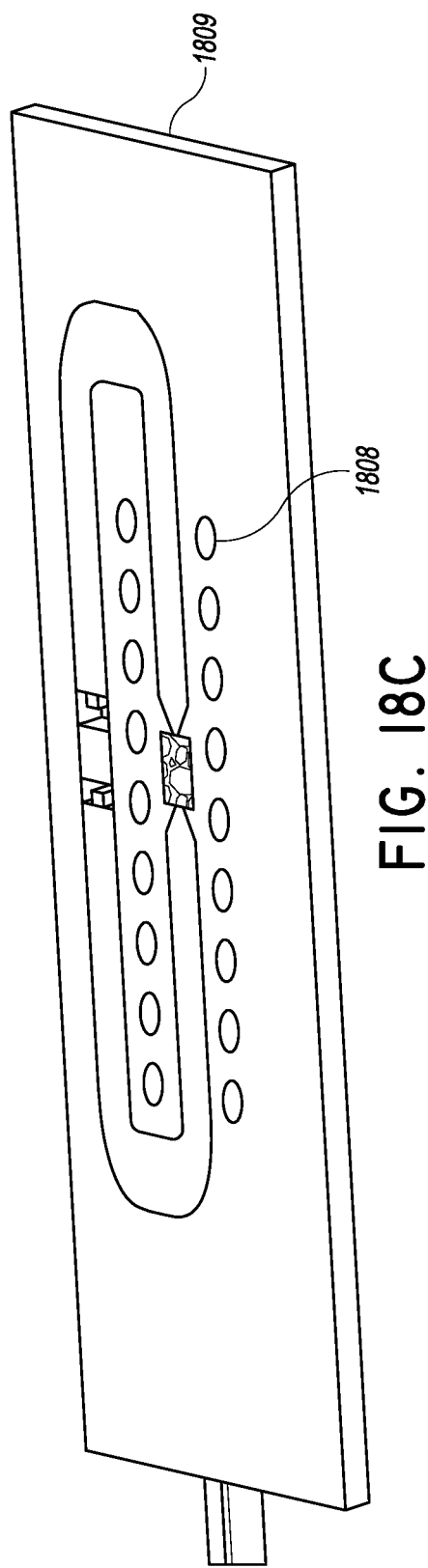

FIGS. 18A through 18C show the thin film NMR probe. FIG. 18A is a front view of the probe. In FIG. 18A, the perforations are formed on the coplanar waveguide grounding plate and close to but not overlap with the constricted section 1803. FIG. 18B is a detailed perspective view of the constricted section. (Not to scale) The conductor 1807 with a constricted slot was formed on top of the substrate 1805, a thin film sample 1806 was placed on top of the conductor and a conductor shield 1804 is placed right above the thin film sample (not shown). FIG. 18C shows that perforations 1808 are formed on the grounding plate 1809. The thin film sample envisaged is 100 μm, but could be thicker or thinner in different applications. The conductor shield confines the RF field inside the thin film sample and serves to improve the filling factor, the efficiency and SNR. If illumination of the sample is needed, the conductor shield can be Indium Tin Oxide (ITO), a kind of transparent conductor.

Example 3. Parallel Analysis Microfluidic NMR Probes

Figure 19:
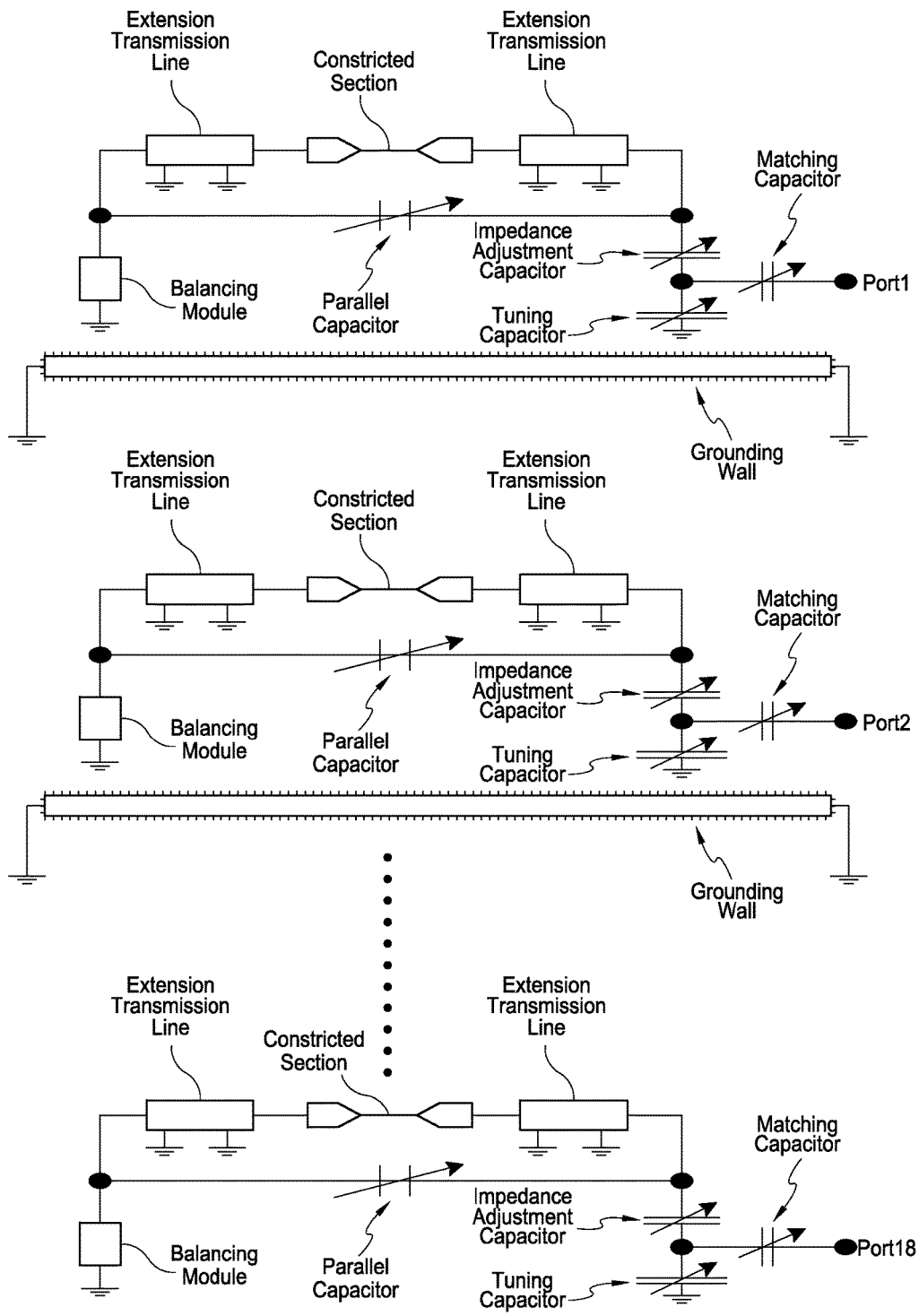
FIG. 19 shows an example of a NMR probe circuit which could be used for parallel analysis of microfluidic samples. In this example, 18 channels (ports) are shown.

An array of probes and microfluidics can be arranged for characterizing multiple samples simultaneously. FIG. 19 shows a circuit of the parallel analysis microfluidic NMR probes. FIG. 19 shows eighteen micro-NMR probes. However, this parallel implementation of the circuit can be extended to accommodate any number of fluidic channels. Each micro-NMR probe works independently. These micro-NMR probes are isolated by the grounding wall to avoid cross talk among them. The grounding wall is grounded.

Figure 20A:
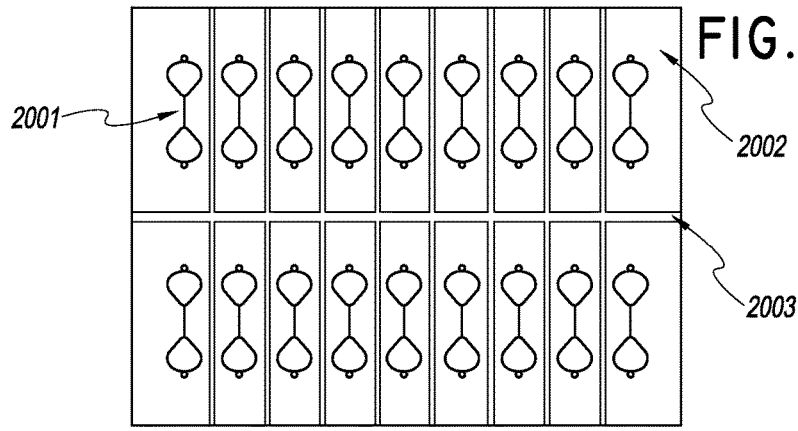
FIGS. 20A through 20C illustrate examples of the laminate of the parallel analysis microfluidic NMR probe design. (20A) The front view of the laminate with 18 micro-NMR probes. (20B) The back view of the laminate. (20C) Perspective view of the laminate.
Figure 20B:
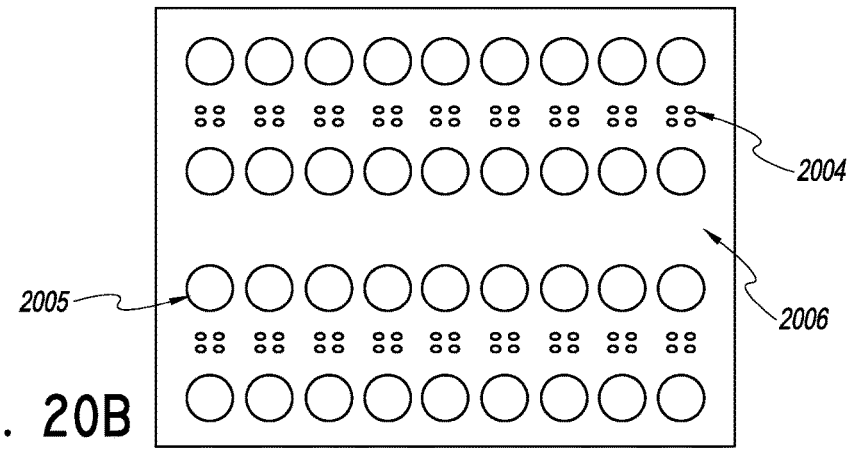
Figure 20C:
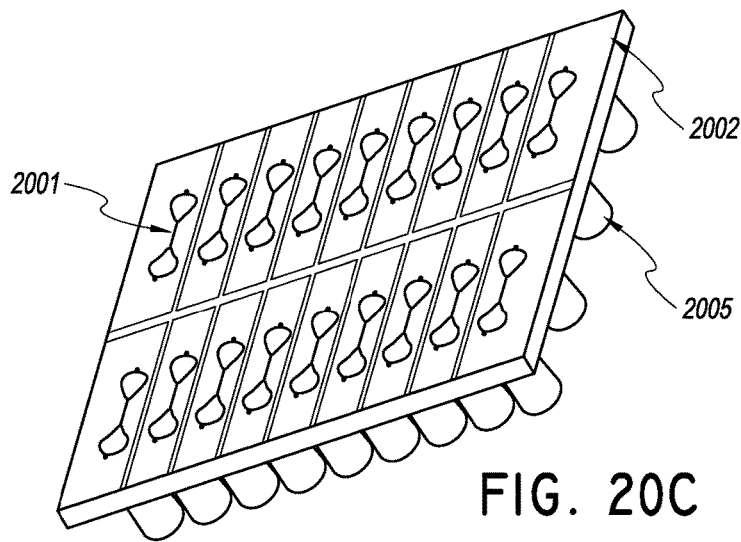

FIGS. 20A through 20C show the laminate of the parallel analysis microfluidic NMR probes. FIG. 20A is a front view of the laminate with an array of micro-NMR probes. Eighteen NMR probes with constricted sections 2001 are placed on top of the substrate 2002 and isolated by the grounding wall 2003. FIG. 20B is a back view of the laminate. Perforations 2004 are formed on the grounding plate 2006. The extension transmission lines 2005 connect the constricted section 2001 to the rest of the NMR probe circuit as shown in FIG. 20C.

Figure 21A:
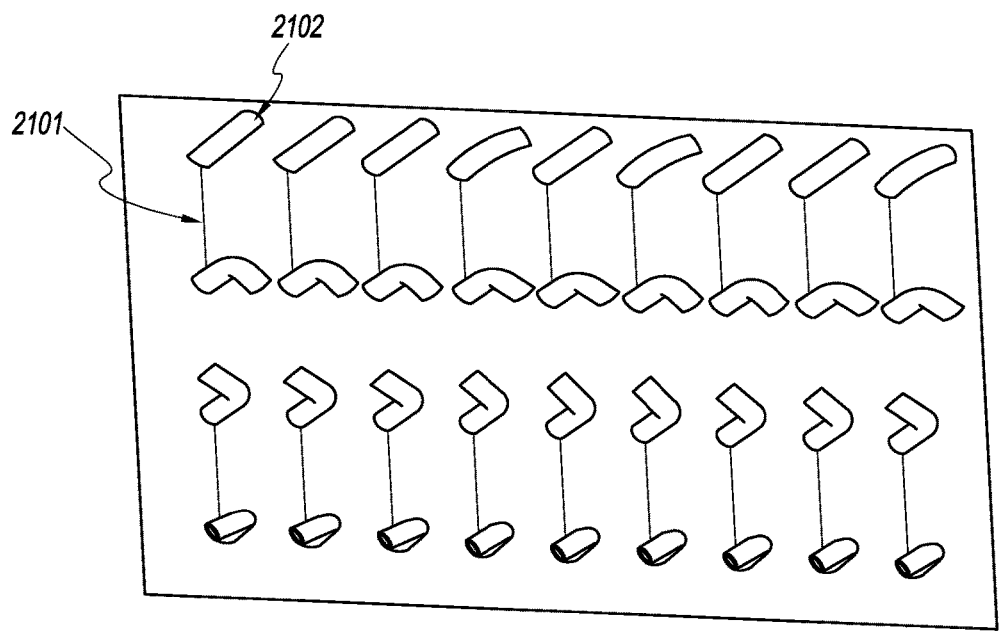
FIGS. 21A and 21B show an example of the parallel analysis microfluidic NMR system. (21A) Microfluidic chip with 18 channels. (21B) The parallel analysis microfluidic NMR system with 18 channels and 18 micro-NMR probes.
Figure 21B:
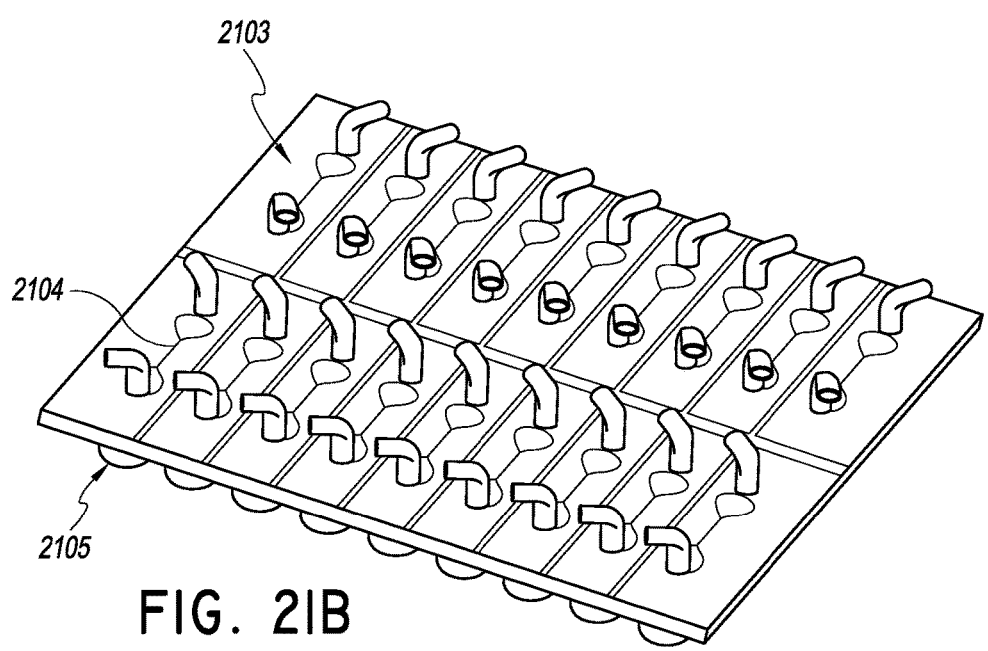

FIGS. 21A and 21B show a parallel analysis microfluidic NMR system. In FIG. 21A, the microfluidic chip has 18 channels 2101 and each channel 2101 is connected to two tygon tubings 2102. In FIG. 21B, the parallel analysis microfluidic NMR system includes the microfluidic chip 2103 with 18 channels and 18 NMR probes 2104 on the NMR probe array 2105. The center of each channel is aligned with the center of the corresponding constricted section. There are two tubings 2101 connected to each microfluidic channel 2101 to function as the inlet and outlet respectively.

Figure 22A:
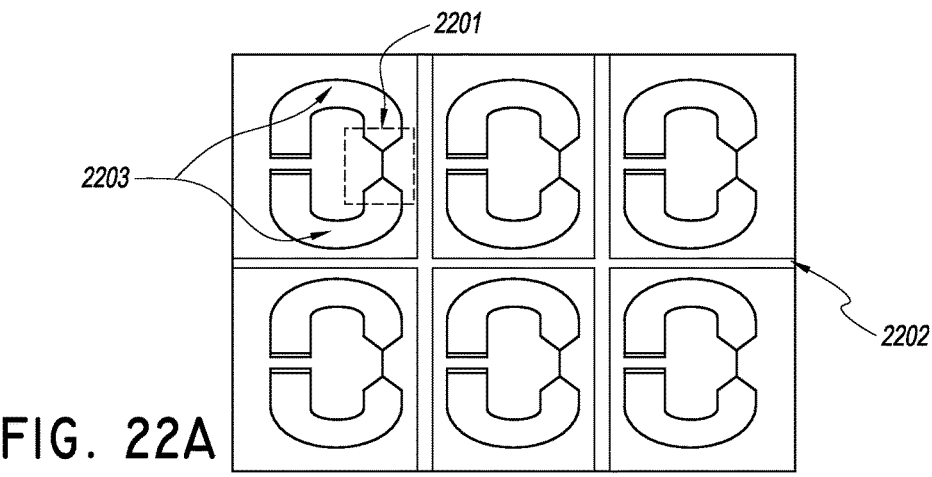
FIGS. 22A through 22C illustrate examples of the laminate of another parallel analysis microfluidic NMR probe design. (22A) The front view of the laminate with 6 micro-NMR probes. (22B) The back view of the laminate. (22C) Perspective view of the laminate.
Figure 22B:
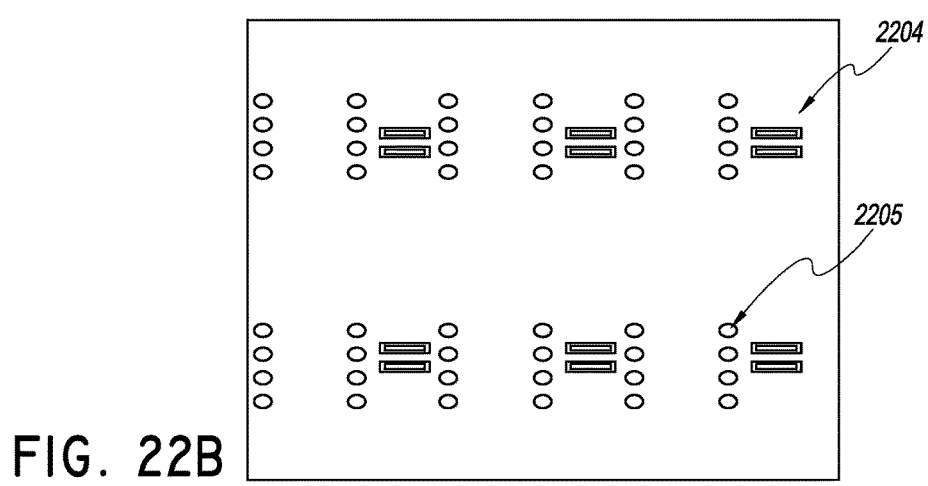
Figure 22C:
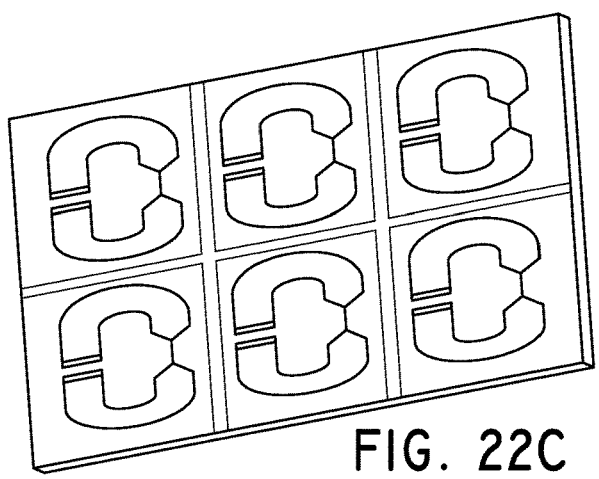

FIGS. 22A through 22C show the laminate of another parallel analysis microfluidic NMR probes. FIG. 22A is a front view of the laminate and shows 6 micro-NMR probes. Each NMR probe has a constricted section 2201 that is connected by the extension transmission lines to the rest of the circuit. The probes are isolated by the grounding wall 2202. FIG. 22B is a rear view of the laminate and shows perforations 2205 formed on the grounding plate 2204. FIG. 22C is a 3D view of the laminate. The parallel analysis can be used for cell sorting, medical diagnosis, or to investigate chemical reaction mechanisms.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A magnetic resonance probe for use in a NMR, MRI, or EPR, comprising
   a resonator;
   a conductor electrically coupled to the resonator and configured to transmit and receive electromagnetic radiation to and from a sample, wherein the conductor comprises one or more cascaded narrowed regions along its longitudinal dimension and a slot within one of the one or more cascaded narrowed regions; and
   an electrical circuit coupled to the conductor and the resonator.

2. The magnetic resonance probe of claim 1, wherein the slot is positioned centered on the narrowest region of the conductor.

3. The magnetic resonance probe of claim 1, wherein the slot is defined by a first wire and a second wire substantially parallel to its longitudinal dimension.

4. The magnetic resonance probe of claim 1, wherein the slot is defined by a first wire and a second wire, the first and the second wires having one or more cascaded narrowed regions.

5. The magnetic resonance probe of claim 1, wherein the slot is defined by a first wire and a second wire, the first and the second wires having one or more intrusions extending laterally inside the slot.

6. The magnetic resonance probe of claim 1, wherein the slot is defined by a first wire and a second wire, the first and the second wires continuously intruding laterally inside the slot.

7. The magnetic resonance probe of claim 1, wherein the resonator is balanced.

8. The magnetic resonance probe of claim 1, wherein the circuit is balanced.

9. The magnetic resonance probe of claim 1, further comprising a ground plate adjacent to the conductor, wherein the ground plate has one or more perforations.

10. The magnetic resonance probe of claim 1, wherein the perforations are positioned around the conductor and spaced from the slot.

11. The magnetic resonance probe of claim 1, further comprising a shimming mechanism to reduce line-width of signal peaks.

12. The magnetic resonance probe of claim 1, wherein a narrowest region of the conductor has a lateral width in a range from about $10\mu$ to $1000\mu$.

13. The magnetic resonance probe of claim 1, wherein a narrowest region of the slot has a lateral width in a range from about $10\mu$ to $1000\mu$.

14. The magnetic resonance probe of claim 1, wherein a lateral width of the conductor at each cascaded narrowed region is decreased by from about 1% to about 90%.

15. The magnetic resonance probe of claim 1, wherein the probe is laminated to a printed circuit board.

16. The magnetic resonance probe of claim 1, comprising
   a plurality of resonators;
   a plurality of elongated conductors electrically coupled to the resonators and configured to transmit and receive electromagnetic radiation to and from one or more samples, wherein each conductor comprises one or more cascaded narrowed regions and a slot within one of the one or more cascaded narrowed regions; and
   an electrical circuit coupled to the conductors and resonators.

17. A NMR, MRI, or EPR apparatus, comprising:
   a magnetic resonance probe, wherein the probe comprises one or more resonators,
      one or more elongated conductors electrically coupled to the resonators and configured to transmit and receive electromagnetic radiation to and from one or more samples, wherein each conductor comprises two or more cascaded narrowed regions and a slot within one of the one or more cascaded narrowed regions, and
      an electrical circuit coupled to the conductors and resonators; and
   one or more microfluidic chips, wherein the microfluidic chip comprises one or more channels configured to transport a sample and is aligned with the slot.

18. The apparatus of claim 17, further comprising a microfluidic element configured to drive a sample through the channels.

19. The apparatus of claim 17, further comprising an automatic adjustment element configured to achieve a balanced magnetic field.

20. The apparatus of claim 17, wherein the slot is positioned centered on the narrowest region of the conductor.

21. The apparatus of claim 17, wherein the slot is defined by a first wire and a second wire substantially parallel to its longitudinal dimension.

22. The apparatus of claim 17, wherein the slot is defined by a first wire and a second wire, the first and the second wires having one or more cascaded narrowed regions.

23. The apparatus of claim 17, wherein the slot is defined by a first wire and a second wire, the first and the second wires having one or more intrusions extending laterally inside the slot.

24. The apparatus of claim 17, wherein the slot is defined by a first wire, the first and the second wires continuously intruding laterally inside the slot.

25. The apparatus of claim 17, wherein the resonator is balanced.

26. The apparatus of claim 17, wherein the circuit is balanced.

27. The apparatus of claim 17, further comprising a ground plate adjacent to the conductor, wherein the ground plate has one or more perforations.

28. The apparatus of claim 17, wherein the perforations are positioned around the conductor and spaced from the slot.

29. The apparatus of claim 17, further comprising a shimming mechanism to reduce line-width of signal peaks.

30. The apparatus of claim 17, wherein the narrowest region of the conductor has a lateral width in a range from about 10µ to 1000µ.

31. The apparatus of claim 17, wherein the narrowest region of the slot has a lateral width in a range from about 10µ to 1000µ.

32. The apparatus of claim 17, wherein a lateral width of the conductor at each cascaded narrowed region is decreased by from about 1% to about 90%.

33. The apparatus of claim 17, comprising
a plurality resonators,
a plurality of elongated conductors electrically coupled to the resonators and configured to transmit and receive electromagnetic radiation to and from one or more samples, wherein each conductor comprises one or more cascaded narrowed regions and a slot within one of the one or more cascaded narrowed regions; and
an electrical circuit coupled to the conductors and resonators.

34. A method of detecting magnetic resonance in a sample, comprising
providing a magnetic resonance probe comprising an elongated conductor, wherein the conductor has one or more cascaded narrowed regions along its longitudinal dimension and a slot within one of the one or more cascaded narrowed regions;
positioning the sample inside or adjacent to the slot;
applying an electrical excitation signal to energize the conductor; and
detecting an electromagnetic signal emanating from the sample.

35. The method of claim 34, wherein the slot is positioned centered on the narrowest region of the conductor.

36. The method of claim 34, wherein the slot is defined by a first wire and a second wire substantially parallel to its longitudinal dimension.

37. The method of claim 34, wherein the slot is defined by a first wire and a second wire, the first and the second wires having one or more cascaded narrowed regions.

38. The method of claim 34, wherein the slot is defined by a first wire and a second wire, the first and the second wires having one or more intrusions extending laterally inside the slot.

39. The method of claim 34, wherein the slot is defined by a first wire, the first and the second wires continuously intruding laterally inside the slot.

40. The method of claim 34, wherein the resonator is balanced.

41. The method of claim 34, further comprising a ground plate adjacent to the conductor, wherein the ground plate has one or more perforations.

42. The method of claim 34, wherein the perforations are positioned around the conductor and spaced from the constricted slot.

43. The method of claim 34, further comprising a shimming mechanism to reduce line-width of signal peaks.

44. The method of claim 34, wherein the narrowest region of the conductor has a lateral width in a range from about 10µ to 1000µ.

45. The method of claim 34, wherein the narrowest region of the slot has a lateral width in a range from about 10µ to 1000µ.

46. The method of claim 34, wherein a lateral width of the conductor at each cascaded narrowed region is decreased by from about 1% to about 90%.

47. A method of analyzing a sample, comprising
providing a magnetic resonance probe comprising an elongated conductor, wherein the conductor comprises one or more cascaded narrowed regions along its longitudinal dimension and a slot within one of the one or more cascaded narrowed regions;
introducing the sample into a microfluidic chip, wherein the microfluidic chip comprises one or more channels configured to transport the sample and is positioned inside or adjacent to the slot;
transporting the sample through the channels of the microfluidic chip;
applying an electromagnetic excitation signal to energize the conductor; and
detecting an electromagnetic signal emanating from the sample.

48. The method of claim 47, wherein the electromagnetic signal emanating from the sample is used to identify the presence of a cancer cell.

49. The method of claim 47, wherein the microfluidic chip is aligned with the slot either manually or automatically.

50. The magnetic resonance probe of claim 1, wherein the conductor is planar.

51. The magnetic resonance probe of claim 1, wherein the slot is a planar constricted slot.

* * * * *